United States Patent
Eriksen et al.

(10) Patent No.: US 8,415,358 B2
(45) Date of Patent: Apr. 9, 2013

(54) PYRAZINE DERIVATIVES AND THEIR USE AS POTASSIUM CHANNEL MODULATORS

(75) Inventors: Birgitte L. Eriksen, Farum (DK); Ulrik Svane Sørensen, Søborg (DK); Charlotte Hougaard, Bagsvaerd (DK); Dan Peters, Malmö (SE); Palle Christophersen, Ballerup (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 12/678,244

(22) PCT Filed: Sep. 16, 2008

(86) PCT No.: PCT/EP2008/062291
§ 371 (c)(1),
(2), (4) Date: Jun. 2, 2010

(87) PCT Pub. No.: WO2009/037247
PCT Pub. Date: Mar. 26, 2009

(65) Prior Publication Data
US 2010/0286161 A1    Nov. 11, 2010

Related U.S. Application Data

(60) Provisional application No. 60/973,255, filed on Sep. 18, 2007.

(30) Foreign Application Priority Data

Sep. 17, 2007  (DK) .................................. 2007 01336

(51) Int. Cl.
*A61K 31/4965* (2006.01)
(52) U.S. Cl.
USPC .... 514/255.05; 544/333; 544/405; 548/373.1
(58) Field of Classification Search ............. 514/255.05; 544/333, 405; 548/373.1
See application file for complete search history.

(56) References Cited

U.S. PATENT DOCUMENTS

| | | | |
|---|---|---|---|
| 2003/0060629 A1 | 3/2003 | Kuo et al. | |
| 2007/0161635 A1* | 7/2007 | Burns et al. | 514/235.5 |
| 2008/0275045 A1 | 11/2008 | Eriksen et al. | |
| 2009/0036475 A1 | 2/2009 | Eriksen et al. | |
| 2009/0306102 A1 | 12/2009 | Eriksen et al. | |
| 2009/0325989 A1 | 12/2009 | Eriksen et al. | |
| 2010/0035934 A1 | 2/2010 | Eriksen et al. | |
| 2010/0105705 A1 | 4/2010 | Eriksen et al. | |
| 2010/0120797 A1 | 5/2010 | Eriksen et al. | |
| 2010/0130516 A1 | 5/2010 | Eriksen et al. | |
| 2010/0152210 A1 | 6/2010 | Eriksen et al. | |
| 2012/0004246 A1 | 1/2012 | Eriksen et al. | |

FOREIGN PATENT DOCUMENTS

| | | | |
|---|---|---|---|
| EP | 1 533 304 A1 | | 5/2005 |
| JP | 10251255 | * | 9/1998 |
| WO | WO 03/099811 A1 | | 12/2003 |
| WO | WO 2005/066156 A1 | | 7/2005 |
| WO | WO 2005/100340 A2 | | 10/2005 |
| WO | WO 2005/121126 A1 | | 12/2005 |
| WO | WO 2006/067466 A2 | | 6/2006 |
| WO | WO 2006/119451 A1 | | 11/2006 |
| WO | WO 2007/008541 A2 | | 1/2007 |
| WO | WO 2008/040753 A1 | | 4/2008 |
| WO | WO 2008/116909 A1 | | 10/2008 |
| WO | WO 2008/116910 A1 | | 10/2008 |
| WO | WO 2008/116911 A1 | | 10/2008 |
| WO | WO 2008/116912 A1 | | 10/2008 |
| WO | WO 2008/116914 A1 | | 10/2008 |

OTHER PUBLICATIONS

Kuo et al. "Synthesis and Discovery of Pyrazine-Pyridine Biheteroaryl as a Novel Series of Potent Vascular Endothelial Growth Factor Receptor-2 Inhibitors", Journal of Medicinal Chemistry, vol. 48, No. 6, 2005, pp. 1886-1900, XP-002509097.

Kuo et al. "Synthesis and Structure-Activity Relationships of Pyrazine-Pyridine Biheteroaryls as Novel, Potent, and Slective Vascular Endothelial Growth Factor Receptor-2 Inhibitors", Journal of Medicinal Chemistry, vol. 48, No. 15, 2005, pp. 4892-4909, XP002509098.

* cited by examiner

*Primary Examiner* — Douglas M Willis
(74) *Attorney, Agent, or Firm* — Birch, Stewart, Kolasch & Birch, LLP

(57) ABSTRACT

Pyrazine compounds of the formula

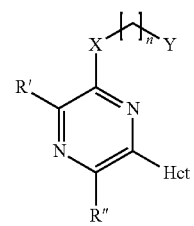

as well as stereoisomers thereof, N-oxides thereof, prodrugs thereof, and pharmaceutically acceptable salts thereof, wherein the variables in the formula are as defined in the specification. The compounds are useful as potassium channel modulating agents. Also, pharmaceutical compositions useful for the treatment or alleviation of diseases or disorders associated with the activity of potassium channels, and methods of using the pharmaceutical compositions.

9 Claims, No Drawings

PYRAZINE DERIVATIVES AND THEIR USE AS POTASSIUM CHANNEL MODULATORS

This application is the National Phase of PCT/EP2008/062291 filed on Sep. 16, 2008, which claims priority under 35 U.S.C.119(e) to U.S. Provisional Application No. 60/973,255 filed on Sep. 18, 2007, and under 35 U.S.C.119(a) to Patent Application No. PA 2007 01336 filed in Denmark on Sep. 17, 2007, all of which are hereby expressly incorporated by reference into the present application.

TECHNICAL FIELD

This invention relates to novel pyrazine derivatives and their use as potassium channel modulating agents. Moreover the invention is directed to pharmaceutical compositions useful for the treatment or alleviation of diseases or disorders associated with the activity of potassium channels.

BACKGROUND ART

Ion channels are transmembrane proteins, which catalyse the transport of inorganic ions across cell membranes. The ion channels participate in processes as diverse as the generation and timing of action potentials, synaptic transmissions, secretion of hormones, contraction of muscles, etc.

All mammalian cells express potassium ($K^+$) channels in their cell membranes, and the channels play a dominant role in the regulation of the membrane potential. In nerve and muscle cells they regulate the frequency and form of the action potential, the release of neurotransmitters, and the degree of broncho- and vasodilation.

From a molecular point of view, the $K^+$ channels represent the largest and most diverse group of ion channels. For an overview they can be divided into five large subfamilies: Voltage-activated $K^+$ channels ($K_v$), long QT related $K^+$ channels (KvLQT), inward rectifiers ($K_{IR}$), two-pore $K^+$ channels ($K_{TP}$), and calcium-activated $K^+$ channels ($K_{ca}$).

The latter group, the $Ca^{2+}$-activated $K^+$ channels, consists of three well-defined subtypes: SK channels, IK channels and BK channels. SK, IK and BK refer to the single-channel conductance (Small, Intermediate and Big conductance K channel). The SK, IK, and BK channels exhibit differences in e.g. voltage- and calcium-sensitivity, pharmacology, distribution and function.

SK channels are present in many central neurons and ganglia, where their primary function is to hyperpolarize nerve cells following one or several action potentials, in order to prevent long trains of epileptogenic activity to occur. The SK channels are also present in several peripheral cells including skeletal muscle, gland cells, liver cells, and T-lymphocytes. The significance of SK channels in normal skeletal muscle is not clear, but their number is significantly increased in denervated muscle, and the large number of SK channels in the muscle of patients with myotonic muscle dystrophia, suggest a role in the pathogenesis of the disease.

Studies indicate that $K^+$ channels may be a therapeutic target in the treatment of a number of diseases including asthma, cystic fibrosis, chronic obstructive pulmonary disease and rhinorrhea, convulsions, vascular spasms, coronary artery spasms, renal disorders, polycystic kidney disease, bladder spasms, overactive bladder, urinary incontinence, bladder outflow obstruction, interstitiel cystitis, irritable bowel syndrome, gastrointestinal dysfunction, secretory diarrhoea, ischaemia, cerebral ischaemia, ischaemic heart disease, angina pectoris, coronary heart disease, traumatic brain injury, psychosis, anxiety, depression, dementia, memory and attention deficits, Alzheimer's disease, dysmenorrhea, narcolepsy, Reynaud's disease, intermittent claudication, Sjogren's syndrome, migraine, pain, arrhythmia, hypertension, absence seizures, myotonic muscle dystrophia, xerostomi, diabetes type II, hyperinsulinemia, premature labour, baldness, cancer and immune suppression.

SUMMARY OF THE INVENTION

The present invention resides in the provision of novel chemical compounds capable of modulating SK channels, or subtypes of SK channels.

Accordingly, in its first aspect, the invention provides novel pyrazine derivatives of Formula I

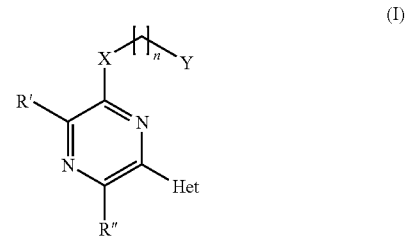

a stereoisomer thereof or a mixture of its stereoisomers, an N-oxide thereof, a prodrug thereof, or a pharmaceutically acceptable salt thereof, wherein n, X, Y, Het, R' and R" are as defined are as defined below.

In another aspect, the invention provides pharmaceutical compositions comprising an effective amount of a pyrazine of the invention.

In further aspects the invention relates to the use of a pyrazine of the invention for use as a medicament, in particular for the manufacture of a medicament for the treatment or alleviation of diseases or disorders associated with the activity of potassium channels, and to method of treatment or alleviation of disorders or conditions responsive to modulation of potassium channels.

DETAILED DISCLOSURE OF THE INVENTION

In its first aspect, the invention provides novel pyrazine derivatives of Formula I

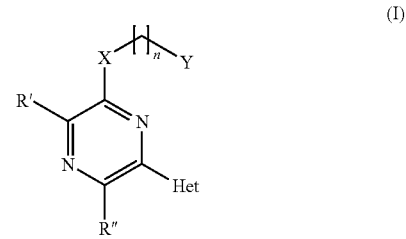

a stereoisomer thereof or a mixture of its stereoisomers, an N-oxide thereof, a prodrug thereof, or a pharmaceutically acceptable salt thereof, wherein
n is 0, 1, 2 or 3;
X represents O, S or $NR^1$; wherein $R^1$ represents hydrogen, alkyl, cycloalkyl, phenyl or benzyl;
Y represents alkyl, cycloalkyl or phenyl; which phenyl may optionally be substituted one or more times with substituents selected from the group consisting of alkyl, cycloalkyl, halo, trifluoromethyl, trifluoromethoxy, hydroxy, alkoxy, cyano, nitro and amino;

Het represents a heterocyclic group selected from pyrazolyl, 1H-pyrazolyl, thiazolyl, pyridinyl, pyrimidinyl, pyrazinyl, indazolyl, benzimidazolyl, which pyrazolyl, 1H-pyrazolyl, thiazolyl, pyridinyl, pyrimidinyl, pyrazinyl, indazolyl and benzimidazolyl may optionally be substituted one or more times with substituents selected from the group consisting of alkyl, hydroxy-alkyl, cycloalkyl, cycloalkyl-alkyl, alkenyl, alkynyl, halo, trifluoromethyl, trifluoromethoxy, hydroxy, alkoxy, alkoxy-carbonyl, carboxy, cyano, nitro, amino, amino-carbonyl, N,N-dialkyl-amino-carbonyl, phenyl and benzyl; and R' and R", independent of each other, represent hydrogen, alkyl, alkoxy-alkyl, amino, amino-alkyl, alkyl-amino, N-alkyl-amino-alkyl, N,N-dialkyl-amino-alkyl, alkyl-carbonyl-amino-alkyl, hydroxy-alkylidenamino, cycloalkyl, phenyl or benzyl.

In one embodiment the pyrazine derivative of the invention is a compound of Formula I, or a pharmaceutically acceptable salt thereof, wherein n is 0, 1, 2 or 3;

X represents O, S or $NR^1$; wherein $R^1$ represents hydrogen, alkyl, cycloalkyl, phenyl or benzyl;

Y represents alkyl, cycloalkyl or phenyl; which phenyl may optionally be substituted one or more times with substituents selected from the group consisting of alkyl, cycloalkyl, halo, trifluoromethyl, trifluoromethoxy, hydroxy, alkoxy, cyano, nitro and amino;

Het represents a heterocyclic group selected from pyrazolyl, 1H-pyrazolyl, thiazolyl, pyridinyl, pyrimidinyl, pyrazinyl and benzimidazolyl, which pyrazolyl, 1H-pyrazolyl, thiazolyl, pyridinyl, pyrimidinyl, pyrazinyl and benzimidazolyl may optionally be substituted one or more times with substituents selected from the group consisting of alkyl, hydroxy-alkyl, cycloalkyl, cycloalkyl-alkyl, alkenyl, alkynyl, halo, trifluoromethyl, trifluoromethoxy, hydroxy, alkoxy, alkoxy-carbonyl, carboxy, cyano, nitro, amino, amino-carbonyl, N,N-dialkyl-amino-carbonyl, phenyl and benzyl; and R' and R", independent of each other, represent hydrogen, alkyl, alkoxy-alkyl, amino, amino-alkyl, alkyl-amino, N-alkyl-amino-alkyl, N,N-dialkyl-amino-alkyl, alkyl-carbonyl-amino-alkyl, hydroxy-alkylidenamino, cycloalkyl, phenyl or benzyl.

In another embodiment the pyrazine derivative of the invention is a compound of Formula I, or a pharmaceutically acceptable salt thereof, wherein n is 0, 1, 2 or 3;

X represents O, S or $NR^1$; wherein $R^1$ represents hydrogen, alkyl, cycloalkyl, phenyl or benzyl;

Y represents alkyl, cycloalkyl or phenyl; which phenyl may optionally be substituted one or more times with substituents selected from the group consisting of alkyl, cycloalkyl, halo, trifluoromethyl, trifluoromethoxy, hydroxy, alkoxy, cyano, nitro and amino;

Het represents a heterocyclic group selected from pyrazolyl, 1H-pyrazolyl, thiazolyl, pyridinyl, pyrimidinyl, pyrazinyl, indazolyl, benzimidazolyl, which pyrazolyl, 1H-pyrazolyl, thiazolyl, pyridinyl, pyrimidinyl, pyrazinyl, indazolyl and benzimidazolyl may optionally be substituted one or more times with substituents selected from the group consisting of alkyl, hydroxy-alkyl, cycloalkyl, cycloalkyl-alkyl, alkenyl, alkynyl, halo, trifluoromethyl, trifluoromethoxy, hydroxy, alkoxy, alkoxy-carbonyl, carboxy, cyano, nitro, amino, amino-carbonyl, N,N-dialkyl-amino-carbonyl, phenyl and benzyl; and R' and R", independent of each other, represent hydrogen, alkyl, alkoxy-alkyl, amino-alkyl, N-alkyl-amino-alkyl, N,N-dialkyl-amino-alkyl, cycloalkyl, phenyl or benzyl.

In another embodiment the pyrazine derivative of the invention is a compound of Formula I, or a pharmaceutically acceptable salt thereof, wherein n is 0, 1, 2 or 3.

In another embodiment n is 0, 1 or 2.

In another embodiment n is 0 or 1.

In another embodiment n is 0.

In another embodiment the pyrazine derivative of the invention is a compound of Formula I, or a pharmaceutically acceptable salt thereof, wherein X represents O, S or $NR^1$; wherein $R^1$ represents hydrogen, alkyl, cycloalkyl, phenyl or benzyl.

In another embodiment X represents O or S.

In another embodiment X represents $NR^1$; wherein $R^1$ represents hydrogen, alkyl, cycloalkyl, phenyl or benzyl.

In another embodiment X represents $NR^1$; wherein $R^1$ represents hydrogen or alkyl.

In another embodiment X represents $NR^1$; wherein $R^1$ represents hydrogen or methyl.

In another embodiment X represents NH.

In another embodiment the pyrazine derivative of the invention is a compound of Formula I, or a pharmaceutically acceptable salt thereof, wherein Y represents alkyl, cycloalkyl or phenyl; which phenyl may optionally be substituted one or more times with substituents selected from the group consisting of alkyl, cycloalkyl, halo, trifluoromethyl, trifluoromethoxy, hydroxy, alkoxy, cyano, nitro and amino.

In another embodiment Y represents cycloalkyl, and in particular cyclohexyl.

In another embodiment Y represents phenyl; which phenyl may optionally be substituted one or more times with substituents selected from the group consisting of alkyl, cycloalkyl, halo, trifluoromethyl, trifluoromethoxy, hydroxy, alkoxy, cyano, nitro and amino.

In another embodiment Y represents phenyl; which phenyl may optionally be substituted one or more times with substituents selected from the group consisting of halo, trifluoromethyl, trifluoromethoxy.

In another embodiment Y represents phenyl; which phenyl may optionally be substituted with halo, trifluoromethyl or trifluoromethoxy.

In another embodiment Y represents phenyl; which phenyl may optionally be substituted with halo, and in particular chloro.

In another embodiment Y represents cycloalkyl, and in particular cyclohexyl, or phenyl, which phenyl may optionally be substituted with halo, and in particular chloro.

In another embodiment the pyrazine derivative of the invention is a compound of Formula I, or a pharmaceutically acceptable salt thereof, wherein Het represents a heterocyclic group selected from pyrazolyl, 1H-pyrazolyl, thiazolyl, pyridinyl, pyrimidinyl, pyrazinyl, indazolyl, benzimidazolyl, which pyrazolyl, 1H-pyrazolyl, thiazolyl, pyridinyl, pyrimidinyl, pyrazinyl, indazolyl and benzimidazolyl may optionally be substituted one or more times with substituents selected from the group consisting of alkyl, hydroxy-alkyl, cycloalkyl, cycloalkyl-alkyl, alkenyl, alkynyl, halo, trifluoromethyl, trifluoromethoxy, hydroxy, alkoxy, alkoxy-carbonyl, carboxy, cyano, nitro, amino, amino-carbonyl, N,N-dialkyl-amino-carbonyl, phenyl and benzyl.

In another embodiment Het represents a heterocyclic group selected from pyrazolyl, 1H-pyrazolyl, thiazolyl, pyridinyl, pyrimidinyl, pyrazinyl and benzimidazolyl, which pyrazolyl, 1H-pyrazolyl, thiazolyl, pyridinyl, pyrimidinyl, pyrazinyl and benzimidazolyl may optionally be substituted one or more times with substituents selected from the group consisting of alkyl, hydroxy-alkyl, cycloalkyl, cycloalkyl-alkyl, alkenyl, alkynyl, halo, trifluoromethyl, trifluoromethoxy, hydroxy, alkoxy, alkoxy-carbonyl, carboxy, cyano, nitro, amino, amino-carbonyl, N,N-dialkyl-amino-carbonyl, phenyl and benzyl.

In another embodiment Het represents a heterocyclic group selected from pyrazolyl, 1H-pyrazolyl, thiazolyl, pyridinyl, pyrimidinyl, pyrazinyl, indazolyl and benzimidazolyl, which pyrazolyl, 1H-pyrazolyl, thiazolyl, pyridinyl, pyrimidinyl, pyrazinyl, indazolyl and benzimidazolyl may optionally be substituted one or two times with substituents selected from the group consisting of alkyl, and in particular methyl, hydroxy, and alkoxy, and in particular methoxy.

In another embodiment Het represents a heterocyclic group selected from pyrazolyl, 1H-pyrazolyl, thiazolyl, pyridinyl, pyrimidinyl, pyrazinyl and benzimidazolyl, which pyrazolyl, 1H-pyrazolyl, thiazolyl, pyridinyl, pyrimidinyl, pyrazinyl and benzimidazolyl may optionally be substituted one or two times with substituents selected from the group consisting of alkyl, and in particular methyl, hydroxy, and alkoxy, and in particular methoxy.

In another embodiment Het represents a heterocyclic group selected from pyrazolyl, 1H-pyrazolyl, thiazolyl, pyridinyl, pyrimidinyl, pyrazinyl, indazolyl and benzimidazolyl, which pyrazolyl, 1H-pyrazolyl, thiazolyl, pyridinyl, pyrimidinyl, pyrazinyl, indazolyl and benzimidazolyl may optionally be substituted one or two times with substituents selected from the group consisting of alkyl, and in particular methyl, and alkoxy, and in particular methoxy.

In another embodiment Het represents a heterocyclic group selected from pyrazolyl, 1H-pyrazolyl, thiazolyl, pyridinyl, pyrimidinyl, pyrazinyl and benzimidazolyl, which pyrazolyl, 1H-pyrazolyl, thiazolyl, pyridinyl, pyrimidinyl, pyrazinyl and benzimidazolyl may optionally be substituted one or two times with substituents selected from the group consisting of alkyl, and in particular methyl, and alkoxy, and in particular methoxy.

In another embodiment Het represents pyrazolyl, which may optionally be substituted one or two times with substituents selected from the group consisting of alkyl, hydroxy-alkyl, cycloalkyl, cycloalkyl-alkyl, alkenyl, alkynyl, halo, trifluoromethyl, trifluoromethoxy, hydroxy, alkoxy, alkoxy-carbonyl, carboxy, cyano, nitro, amino, amino-carbonyl, N,N-dialkyl-amino-carbonyl, phenyl and benzyl.

In another embodiment Het represents a pyrazolyl group selected from pyrazol-1-yl and pyrazol-3-yl, which pyrazolyl may optionally be substituted one or two times with substituents selected from the group consisting of alkyl and alkoxy.

In another embodiment Het represents a pyrazolyl group selected from pyrazol-1-yl and pyrazol-3-yl, which may optionally be substituted one or two times with alkyl, and in particular methyl.

In another embodiment Het represents a pyrazolyl group selected from pyrazol-1-yl and pyrazol-3-yl.

In another embodiment Het represents a pyrazolyl group selected from pyrazol-1-yl and pyrazol-3-yl, which is substituted with alkyl, and in particular methyl.

In another embodiment Het represents a pyrazolyl group selected from pyrazol-1-yl and pyrazol-3-yl, which is substituted two times with alkyl, and in particular methyl.

In another embodiment Het represents 1H-pyrazolyl, which 1H-pyrazol-3-yl may optionally be substituted one or two times with substituents selected from the group consisting of alkyl and alkoxy.

In another embodiment Het represents 1H-pyrazol-3-yl, which 1H-pyrazol-3-yl may optionally be substituted one or two times with substituents selected from the group consisting of alkyl and alkoxy.

In another embodiment Het represents 1H-pyrazol-3-yl.

In another embodiment Het represents 1H-pyrazol-3-yl, substituted one time with a substituent selected from the group consisting of alkyl and alkoxy.

In another embodiment Het represents 1H-pyrazol-3-yl, which 1H-pyrazol-3-yl substituted two times with substituents selected from the group consisting of alkyl and alkoxy.

In another embodiment Het represents thiazolyl, which may optionally be substituted one or two times with substituents selected from the group consisting of alkyl, hydroxy-alkyl, cycloalkyl, cycloalkyl-alkyl, alkenyl, alkynyl, halo, trifluoromethyl, trifluoromethoxy, hydroxy, alkoxy, alkoxy-carbonyl, carboxy, cyano, nitro, amino, amino-carbonyl, N,N-dialkyl-amino-carbonyl, phenyl and benzyl.

In another embodiment Het represents thiazolyl, optionally substituted one or two times with substituents alkyl.

In another embodiment Het represents thiazolyl.

In another embodiment Het represents pyridinyl, which may optionally be substituted one or two times with substituents selected from the group consisting of alkyl, hydroxy-alkyl, cycloalkyl, cycloalkyl-alkyl, alkenyl, alkynyl, halo, trifluoromethyl, trifluoromethoxy, hydroxy, alkoxy, alkoxy-carbonyl, carboxy, cyano, nitro, amino, amino-carbonyl, N,N-dialkyl-amino-carbonyl, phenyl and benzyl.

In another embodiment Het represents pyridinyl, which may optionally be substituted with alkyl, hydroxy or alkoxy.

In another embodiment Het represents pyridinyl, which may optionally be substituted with alkyl, and in particular methyl, or alkoxy, and in particular methoxy.

In another embodiment Het represents a pyridin-2-yl group, which pyridinyl may optionally be substituted with alkyl, and in particular methyl, or alkoxy, and in particular methoxy.

In another embodiment Het represents pyrimidinyl, which may optionally be substituted one or two times with substituents selected from the group consisting of alkyl, hydroxy-alkyl, cycloalkyl, cycloalkyl-alkyl, alkenyl, alkynyl, halo, trifluoromethyl, trifluoromethoxy, hydroxy, alkoxy, alkoxy-carbonyl, carboxy, cyano, nitro, amino, amino-carbonyl, N,N-dialkyl-amino-carbonyl, phenyl and benzyl.

In another embodiment Het represents pyrimidinyl, which may optionally be substituted with alkyl or alkoxy.

In another embodiment Het represents pyrimidinyl.

In another embodiment Het represents pyrazinyl, which may optionally be substituted one or two times with substituents selected from the group consisting of alkyl, hydroxy-alkyl, cycloalkyl, cycloalkyl-alkyl, alkenyl, alkynyl, halo, trifluoromethyl, trifluoromethoxy, hydroxy, alkoxy, alkoxy-carbonyl, carboxy, cyano, nitro, amino, amino-carbonyl, N,N-dialkyl-amino-carbonyl, phenyl and benzyl.

In another embodiment Het represents pyrazinyl, which may optionally be substituted with alkyl or alkoxy.

In another embodiment Het represents pyrazinyl.

In another embodiment Het represents indazolyl, which indazolyl may optionally be substituted one or two times with substituents selected from the group consisting of alkyl and alkoxy.

In another embodiment Het represents an indazolyl selected from 1H-indazolyl and 2H-indazolyl, which indazolyl may optionally be substituted one or two times with substituents selected from the group consisting of alkyl and alkoxy.

In another embodiment Het represents an indazolyl selected from 1H-indazolyl and 2H-indazolyl.

In another embodiment Het represents benzimidazolyl, which benzimidazolyl may optionally be substituted one or two times with substituents selected from the group consisting of alkyl and alkoxy.

In another embodiment Het represents 1H-benzimidazolyl, which 1H-benz-imidazolyl may optionally be substituted one or two times with substituents selected from the group consisting of alkyl and alkoxy.

In another embodiment Het represents 1H-benzimidazolyl, which 1H-benz-imidazolyl may optionally be substituted with substituents selected from the group consisting of alkyl, and in particular methyl.

In another embodiment the pyrazine derivative of the invention is a compound of Formula I, or a pharmaceutically acceptable salt thereof, wherein R' and R", independent of each other, represent hydrogen, alkyl, alkoxy-alkyl, amino, amino-alkyl, alkyl-amino, N-alkyl-amino-alkyl, N,N-dialkyl-amino-alkyl, alkyl-carbonyl-amino-alkyl, hydroxy-alkylidenamino, cycloalkyl, phenyl or benzyl.

In another embodiment R' and R", independent of each other, represent hydrogen, alkyl, alkoxy-alkyl, amino-alkyl, N-alkyl-amino-alkyl, N,N-dialkyl-amino-alkyl, cycloalkyl, phenyl or benzyl.

In another embodiment R' and R", independent of each other, represent hydrogen, alkoxy-alkyl, amino-alkyl, N-alkyl-amino-alkyl or N,N-dialkyl-amino-alkyl.

In another embodiment R' and R" both represent hydrogen.

In another embodiment R' represents alkoxy-alkyl, amino-alkyl, N-alkyl-amino-alkyl or N,N-dialkyl-amino-alkyl; and R" represents hydrogen.

In another embodiment R' represents alkoxy-alkyl, and in particular methoxymethyl; and R" represents hydrogen.

In another embodiment R' represents N-alkyl-amino-alkyl, and in particular N-methyl-amino-methyl; and R" represents hydrogen.

In another embodiment R' represents N,N-dialkyl-amino-alkyl, and in particular N,N-dimethyl-amino-methyl; and R" represents hydrogen.

In another embodiment R' and R", independent of each other, represent hydrogen, amino, alkyl-amino, alkyl-carbonyl-amino-alkyl or hydroxy-alkylidenamino.

In another embodiment R' and R", independent of each other, represent hydrogen and/or amino.

In another embodiment R' and R", independent of each other, represent hydrogen and/or alkyl-amino.

In another embodiment R' and R", independent of each other, represent hydrogen and/or alkyl-carbonyl-amino-alkyl.

In another embodiment R' and R", independent of each other, represent hydrogen and/or hydroxy-alkylidenamino.

In another embodiment the pyrazine derivative of the invention is
(4-Chloro-phenyl)-(6-pyrazol-1-yl-pyrazin-2-yl)-amine;
(4-Chloro-phenyl)-(6-indazol-2-yl-pyrazin-2-yl)-amine;
(4-Chloro-phenyl)-(6-indazol-1-yl-pyrazin-2-yl)-amine;
Cyclohexyl-[6-(3,5-dimethyl-pyrazol-1-yl)-pyrazin-2-yl]-amine;
(4-Chloro-phenyl)-[6-(3,5-dimethyl-pyrazol-1-yl) -pyrazin-2-yl]-amine;
(4-Chloro-phenyl)-[6-(6-methyl-pyridin-2-yl)-pyrazin-2-yl]-amine;
(4-Chloro-phenyl)-[6-(6-methoxy-pyridin-2-yl)-pyrazin-2-yl]-amine;
(4-Chloro-phenyl)-(6-pyridin-2-yl-pyrazin-2-yl)-amine;
(4-Chloro-phenyl)-(6-thiazol-2-yl-pyrazin-2-yl)-amine;
(4-Chloro-phenyl)-(6-pyrimidin-2-yl-pyrazin-2-yl)-amine;
[2,2']Bipyrazinyl-6-yl-(4-chloro-phenyl)-amine;
(4-Chloro-phenyl)-[6-(1H-pyrazol-3-yl)-pyrazin-2-yl]amine;
(4-Chloro-phenyl)-[6-(3-methoxy-pyridin-2-yl)-pyrazin-2-yl]-amine;
(4-Chloro-phenyl)-[6-(1-methyl-1H-benzoimidazol-2-yl)-pyrazin-2-yl]-amine;
(4-Chloro-phenyl)-[3-dimethylaminomethyl-6-(3,5-dimethyl-pyrazol-1-yl)-pyrazin-2-yl]-amine;
(4-Chloro-phenyl)-[6-(3,5-dimethyl-pyrazol-1-yl)-3-methylaminomethyl-pyrazin-2-yl]-amine;
(4-Chloro-phenyl)-[5-dimethylaminomethyl-6-(3,5-dimethyl-pyrazol-1-yl)-pyrazin-2-yl]-amine;
(4-Chloro-phenyl)-[6-(3,5-dimethyl-pyrazol-1-yl)-5-methylaminomethyl-pyrazin-2-yl]-amine;
(4-Chloro-phenyl)-[6-(3,5-dimethyl-pyrazol-1-yl)-3-methoxymethyl-pyrazin-2-yl]-amine; or
[3-Aminomethyl-6-(3,5-dimethyl-pyrazol-1-yl)-pyrazin-2-yl]-(4-chloro-phenyl)-amine; or
a stereoisomer thereof or a mixture of its stereoisomers, an N-oxide thereof, a prodrug thereof, or a pharmaceutically acceptable salt thereof.

In another embodiment the pyrazine derivative of the invention is
(4-Chloro-phenyl)-[6-(3,5-dimethyl-pyrazol-1-yl)-5-methoxymethyl-pyrazin-2-yl]-amine;
3-(4-Chloro-phenylamino)-5-(3,5-dimethyl-pyrazol-1-yl)-pyrazine-2-carbaldehyde oxime;
[5-Aminomethyl-6-(3,5-dimethyl-pyrazol-1-yl)-pyrazin-2-yl]-(4-chloro-phenyl)-amine;
N-[3-(4-Chloro-phenylamino)-5-(3,5-dimethyl-pyrazol-1-yl)-pyrazin-2-ylmethyl]-acetamide;
N-[5-(4-Chloro-phenylamino)-3-(3,5-dimethyl-pyrazol-1-yl)-pyrazin-2-ylmethyl]-acetamide;
5-(4-Chloro-phenylamino)-3-(3,5-dimethyl-pyrazol-1-yl)-pyrazine-2-amine;
5-(4-Chloro-phenylamino)-3-(3,5-dimethyl-pyrazol-1-yl)-2-ethylamino-pyrazine; or
a stereoisomer thereof or a mixture of its stereoisomers, an N-oxide thereof, a prodrug thereof, or a pharmaceutically acceptable salt thereof.

Any combination of two or more of the embodiments described herein is considered within the scope of the present invention.

Definition of Substituents

In the context of this invention halo represents fluoro, chloro, bromo or iodo. In the context of this invention an alkyl group designates a univalent saturated, straight or branched hydrocarbon chain. The hydrocarbon chain may contain of from one to eighteen carbon atoms ($C_{1-18}$-alkyl), e.g. from one to six carbon atoms ($C_{1-6}$-alkyl; lower alkyl), including pentyl, isopentyl, neopentyl, tertiary pentyl, hexyl and isohexyl. In another embodiment alkyl represents a $C_{1-4}$-alkyl group, including butyl, isobutyl, secondary butyl, and tertiary butyl. In another embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In one embodiment the alkenyl group of the invention comprises of from two to eight carbon atoms ($C_{2-8}$-alkenyl), in another embodiment from two to six carbon atoms ($C_{2-6}$-alkenyl), including at least one double bond. In another embodiment the alkenyl group of the invention is ethenyl; 1- or 2-propenyl; 1-, 2- or 3-butenyl, or 1,3-butenyl; 1-, 2-, 3-, 4- or 5-hexenyl, or 1,3-hexenyl, or 1,3,5-hexenyl; 1-, 2-, 3-, 4-, 5-, 6-, or 7-octenyl, or 1,3-octenyl, or 1,3,5-octenyl, or 1,3,5,7-octenyl.

In the context of this invention an alkynyl group designates a straight or branched carbon chain containing one or more triple bonds, including di-ynes, tri-ynes and poly-ynes. In one embodiment the alkynyl group of the invention comprises of from two to eight carbon atoms ($C_{2-8}$-alkynyl), in another embodiment from two to six carbon atoms ($C_{2-6}$-alkynyl), including at least one triple bond. In another embodiment the alkynyl group of the invention is ethynyl; 1-, or 2-propynyl; 1-, 2-, or 3-butynyl, or 1,3-butadiynyl; 1-, 2-, 3-, 4-pentynyl, or 1,3-pentadiynyl; 1-, 2-, 3-, 4-, or 5-hexynyl, or 1,3-hexadiynyl or 1,3,5-hexatriynyl; 1-, 2-, 3-, 4-, 5- or 6-heptynyl, or 1,3-heptdiynyl, or 1,3,5-hepttriynyl; 1-, 2-, 3-, 4-, 5-, 6- or 7-octynyl, or 1,3-octdiynyl, or 1,3,5-octtriynyl, or 1,3,5,7-octtetraynyl.

In the context of this invention a hydroxy-alkyl group designates an alkyl group as defined above, which hydroxy-alkyl group is substituted with one or more hydroxy groups. Examples of hydroxy-alkyl groups of the invention include 2-hydroxy-ethyl, 3-hydroxy-propyl, 4-hydroxy-butyl, 5-hydroxy-pentyl and 6-hydroxy-hexyl.

In the context of this invention a cycloalkyl group designates a cyclic alkyl group, e.g. containing of from three to ten carbon atoms ($C_{3-10}$-cycloalkyl), e.g. from three to eight carbon atoms ($C_{3-8}$-cycloalkyl), including cyclopropyl, cyclobutyl, cyclopentyl, cyclohexyl, cycloheptyl and cyclooctyl.

In the context of this invention a cycloalkyl-alkyl group designates a cycloalkyl group as defined above, which cycloalkyl group is substituted on an alkyl group as also defined above. Examples of cycloalkyl-alkyl groups of the invention include cyclopropylmethyl and cyclopropylethyl.

In the context of this invention an alkoxy group designates an "alkyl-O—" group, wherein alkyl is as defined above. Examples of alkoxy groups of the invention include methoxy and ethoxy.

In the context of this invention an alkoxy-alkyl group designates an "alkyl-O-alkyl-" group, wherein alkyl is as defined above. Examples of alkoxy-alkyl groups of the invention include methoxy-methyl, methoxy-ethyl, ethoxy-methyl, and ethoxy-ethyl.

In the context of this invention an alkoxy-carbonyl group designates an "alkyl-O—CO—" group, wherein alkyl is as defined above. Examples of alkoxy-carbonyl groups of the invention include the methyl-, ethyl- and propyl-ester group.

In the context of this invention an alkyl-carbonyl-amino-alkyl group designates an alkyl-C(=O)—NH-alkyl- group.

In the context of this invention an alkyl-amino group designates a (primary) amino group substituted with an alkyl group as defined above.

In the context of this invention an amino-alkyl group designates an alkyl group as defined above, substituted with a (primary) amino group.

In the context of this invention an N-alkyl-amino-alkyl group designates an alkyl group as defined above, substituted with a (secondary) amino group, which amino group again is substituted with an alkyl group. Examples of N-alkyl-amino-alkyl groups of the invention include N-methyl-amino-methyl, N-methyl-amino-ethyl, N-ethyl-amino-methyl and N-ethyl-amino-ethyl.

In the context of this invention an N,N-dialkyl-amino-carbonyl group designates a (tertiary) amino-carbonyl group, disubstituted with alkyl groups as defined above.

In the context of this invention an N,N-dialkyl-amino-alkyl group designates a (tertiary) amino-alkyl group, disubstituted with alkyl groups as defined above. Examples of N,N-dialkyl-amino-alkyl groups of the invention include N,N-dimethyl-amino-methyl, N,N-dimethyl-amino-ethyl, N,N-diethyl-amino-methyl and N,N-diethyl-amino-ethyl.

In the context of this invention an hydroxy-alkylidenamino group designates an hydroxyl-N=alkyl group.

Isomers

The pyrazine derivatives of the present invention may exist in different stereoisomeric forms, including enantiomers, diastereomers, as well as geometric isomers (cis-trans isomers). The invention includes all such isomers and any mixtures thereof including racemic mixtures.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Moreover, some of the chemical compounds of the invention being oximes, may thus exist in two forms, syn- and anti-form (Z- and E-form), depending on the arrangement of the substituents around the —C=N— double bond. A chemical compound of the present invention may thus be the syn- or the anti-form (Z— and E-form), or it may be a mixture hereof.

Pharmaceutically Acceptable Salts

The pyrazine derivatives of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulfonate derived from benzenesulfonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphthalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a pyrazine derivative of the invention and its pharmaceutically acceptable acid addition salt.

Metal salts of a chemical compound of the invention include alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

The pyrazine derivative of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Methods of Preparation

The pyrazine derivatives of the invention may be prepared by conventional methods of chemical synthesis, e.g. those described in the working examples. The starting materials for the processes described in the present application are known or may readily be prepared by conventional methods from commercially available chemicals.

The end products of the reactions described herein may be isolated by conventional techniques, e.g. by extraction, crystallisation, distillation, chromatography, etc.

Biological Activity

The pyrazine derivatives of the invention have been subjected to in vitro experiments and found particularly useful as potassium channel modulating agents. More particularly the compounds of the invention are capable of selectively modulating SK1, SK2 and/or SK3 channels.

Therefore, in another aspect, the invention relates to pyrazine derivatives of the invention for use as a medicament, and in particular to the use of a pyrazine derivative of the invention for the manufacture of medicaments, which medicament may be useful for the treatment or alleviation of a disease or a disorder associated with the activity of potassium channels, in particular SK channels, more particularly SK1, SK2 and/or SK3 channels.

In one embodiment, the disease or a disorder associated with the activity of potassium channels is a respiratory disease, epilepsy, convulsions, seizures, absence seizures, vascular spasms, coronary artery spasms, renal disorders, polycystic kidney disease, bladder spasms, overactive bladder (OAB), urinary incontinence, bladder outflow obstruction, interstitiel cystitis (IC), erectile dysfunction, gastrointestinal dysfunction, secretory diarrhoea, ischaemia, cerebral ischaemia, ischaemic heart disease, angina pectoris, coronary heart disease, autism, ataxia, traumatic brain injury, Parkinson's disease, dyskinesia, bipolar disorder, psychosis, schizophrenia, anxiety, depression, mania, mood disorders, dementia, memory and attention deficits, Alzheimer's disease, amyotrophic lateral sclerosis (ALS), dysmenorrhea, narcolepsy, Reynaud's disease, intermittent claudication, Sjogren's syndrome, arrhythmia, hypertension, myotonic muscle dystrophia, spasticity, xerostomi, diabetes type II, hyperinsulinemia, premature labour, hair loss, cancer, irritable bowel syndrome (IBS), immune suppression, migraine or pain, e.g. pelvic pain or abdominal pain, addiction, e.g. drug addiction, drug abuse, cocaine abuse, nicotine abuse, tobacco abuse, alcohol addiction or alcoholism, or withdrawal symptoms, or withdrawal symptoms caused by the termination of abuse of chemical substances, in particular opioids, heroin, cocaine and morphine, benzodiazepines and benzodiazepine-like drugs, and alcohol.

In another embodiment the disease or a disorder associated with the activity of potassium channels is a respiratory disease, urinary incontinence, erectile dysfunction, anxiety, epilepsy, psychosis, schizophrenia, amyotrophic lateral sclerosis (ALS) or pain.

In another embodiment the disease or a disorder associated with the activity of potassium channels is a respiratory disease, in particular asthma, cystic fibrosis, chronic obstructive pulmonary disease (COPD) or rhinorrhea.

In another embodiment the disease or a disorder associated with the activity of potassium channels is overactive bladder, e.g. urinary incontinence.

In another embodiment the disease or a disorder associated with the activity of potassium channels is epilepsy, seizures, absence seizures or convulsions.

In another embodiment the disease or a disorder associated with the activity of potassium channels is schizophrenia.

In another embodiment the disease or a disorder associated with the activity of potassium channels is addiction.

In another embodiment the disease or a disorder associated with the activity of potassium channels is Parkinson's disease.

In another embodiment the disease or a disorder associated with the activity of potassium channels is pain.

The compounds tested showed a biological activity in the micromolar and sub-micromolar range, i.e. of from below 1 to above 100 µM. Compounds of the invention show a biological activity determined as described herein in the in the sub-micromolar and micromolar range, i.e. of from below 0.1 to about 10 µM.

Pharmaceutical Compositions

In yet another aspect the invention provides novel pharmaceutical compositions comprising a therapeutically effective amount of the pyrazine derivatives of the invention.

While a pyrazine derivative of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers and/or diluents.

In a preferred embodiment, the invention provides pharmaceutical compositions comprising the pyrazine derivative of the invention, or a pharmaceutically acceptable salt or derivative thereof, together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The pyrazine derivative of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The pyrazine derivative according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the chemical compound according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions which exhibit large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated and the route of administration, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Examples of ranges are from about 0.1 µg/kg to about 10 mg/kg/day i.v., and from about 1 µg/kg to about 100 mg/kg/day p.o.

Methods of Therapy

In another aspect the invention provides a method for the prevention, treatment or alleviation of a disease or a disorder or a condition of a living animal body, including a human, which disease, disorder or condition is responsive to modulation of potassium channels, in particular SK channels, and which method comprises comprising administering to such a living animal body, including a human, in need thereof a therapeutically-effective amount of a pyrazine derivative of the invention.

The indications contemplated according to the invention are those stated above.

It is at present contemplated that suitable dosage ranges are 0.1 to 1000 milligrams daily, 10-500 milligrams daily, and 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Examples of are from about 0.001 to about 1 mg/kg i.v. and from about 0.1 to about 10 mg/kg p.o.

EXAMPLES

The invention is further illustrated with reference to the following examples, which are not intended to be in any way limiting to the scope of the invention as claimed.

Example 1

(4-Chloro-phenyl)-(6-chloro-pyrazin-2-yl)-amine
(Intermediate Compound)

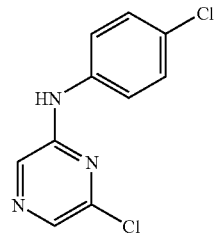 [SMILES: Clc1ccc(Nc2cncc(Cl)n2)cc1]

A mixture of 2,6-dichloropyrazine (2.0 g, 13.4 mmol), 4-chloroaniline (1.88 g, 14.8 mmol) and sodium tert-butoxide (1.71 g, 17.6 mmol) in toluene (45 mL) were degassed with argon for 20 minutes. (±)-2,2'-Bis(diphenylphosphino-)1,1'-binaphthalene ((±)-BINAP) (502 mg, 0.81 mmol) and palladium(II)-acetate (90.4 mg, 0.40 mmol) were added followed by degassing for 5 minutes. The reaction mixture was stirred at 100° C. over night. The mixture was filtrated and the filtrate evaporated. Flash chromatography (ethyl acetate/heptane as eluent) gave (4-chloro-phenyl)-(6-chloro-pyrazin-2-yl)-amine (628 mg, 18%) as a brown oil.

(6-Chloro-pyrazin-2-yl)-cyclohexylamine
(Intermediate Compound)

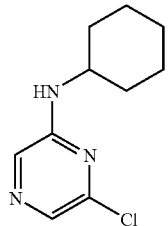 [SMILES: Clc1cncc(NC2CCCCC2)n1]

Was prepared according to Example 1 from 2,6-dichloro-pyrazine and cyclohexylamine.

Example 2

(4-Chloro-phenyl)-(6-chloro-pyrazin-2-yl)-carbamic acid tert-butyl ester (Intermediate Compound)

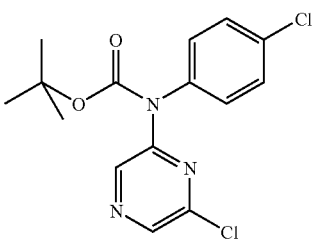 [SMILES: CC(C)(C)OC(=O)N(c1ccc(Cl)cc1)c1cncc(Cl)n1]

A mixture of (4-chloro-phenyl)-(6-chloro-pyrazin-2-yl)-amine (628 mg, 2.62 mmol), 4-(dimethylamino)pyridine (64 mg, 0.52 mmol) and di-tert-butyl dicarbonate (1.73 g, 7.85 mmol) in tetrahydrofuran (50 mL) was heated to reflux for one hour. Evaporation followed by flash chromatography (ethyl acetate/heptane as eluent) gave (4-chloro-phenyl)-(6-chloro-pyrazin-2-yl)-carbamic acid tert-butyl ester (694 mg, 78%) as a brown oil.

Example 3

(4-Chloro-phenyl)-(6-pyrazol-1-yl-pyrazin-2-yl)-amine (Compound 3)

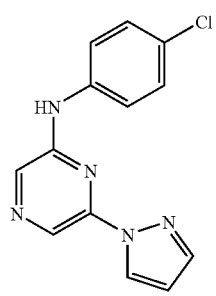 [SMILES: Clc1ccc(Nc2cncc(-n3cccn3)n2)cc1]

Sodium hydride (60% in mineral oil, 156 mg, 3.90 mmol) was added to a suspension of pyrazole (260 mg, 3.82 mmol) in N,N-dimethylformamide (5 mL) and the mixture was heated to 50° C. for 20 minutes. (4-Chloro-phenyl)-(6-chloro-pyrazin-2-yl)-carbamic acid tert-butyl ester (260 mg, 0.76 mmol) was added and stirring was continued for 30 minutes at the same temperature. The temperature was raised to 100° C. and the mixture was stirred overnight. The reaction mixture was quenched with brine and extracted with ethyl acetate (4×15 mL). The combined organic phases were washed with brine, dried over anhydrous sodium sulphate, filtrated and evaporated to give the crude product. Flash chromatography (ethyl acetate/heptane as eluent) gave (4-chloro-phenyl)-(6-pyrazol-1-yl-pyrazin-2-yl)-amine (56 mg, 27%) as a yellow solid.

Mp.=155-157° C. LC-ESI-HRMS of [M+H]+ shows 272.0706 Da. Calc. 272.070298 Da, dev. 1.1 ppm.

(4-Chloro-phenyl)-(6-indazol-2-yl-pyrazin-2-yl)-amine (Compound 3.1); and (4-Chloro-phenyl)-(6-indazol-1-yl-pyrazin-2-yl)-amine (Compound 3.2)

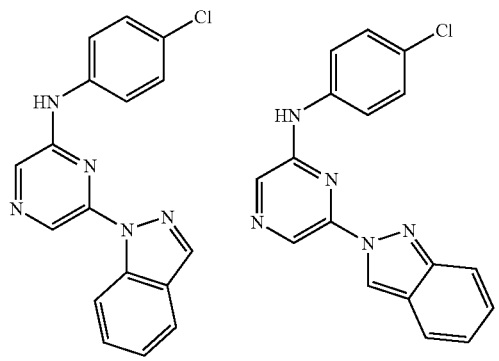 [SMILES: Clc1ccc(Nc2cncc(-n3ncc4ccccc43)n2)cc1 ; Clc1ccc(Nc2cncc(-n3cc4ccccc4n3)n2)cc1]

Were prepared according to Example 3 from (4-chloro-phenyl)-(6-chloro-pyrazin-2-yl)-carbamic acid tert-butyl ester and indazole.

(4-Chloro-phenyl)-(6-indazol-2-yl-pyrazin-2-yl)-amine; Mp.=249-252° C. LC-ESI-HRMS of [M+H]+ shows 322.085 Da. Calc. 322.085948 Da, dev. −2.9 ppm.

(4-Chloro-phenyl)-(6-indazol-1-yl-pyrazin-2-yl)-amine; Mp.=204-207° C. LC-ESI-HRMS of [M+H]+ shows 322.0864 Da. Calc. 322.085948 Da, dev. 1.4 ppm.

Cyclohexyl-[6-(3,5-dimethyl-pyrazol-1-yl)-pyrazin-2-yl]-amine (Compound 3.3)

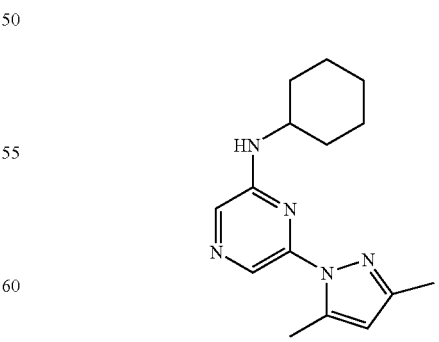

Was prepared according to Example 3 from (6-chloro-pyrazin-2-yl)-cyclohexylamine and 3,5-dimethylpyrazole.

Mp.=115.2-116.8° C. LC-ESI-HRMS of [M+H]+ shows 272.1875 Da. Calc. 272.18752 Da, dev. −0.1 ppm.

2-Chloro-6-(3,5-dimethyl-pyrazol-1-yl)-pyrazine (Intermediate Compound)

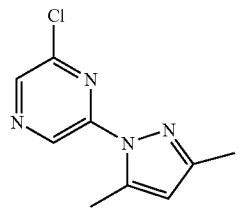

Was prepared according to Example 3 from 2,6-dichloropyrazine and 3,5-dimethylpyrazole.

Example 4

(4-Chloro-phenyl)-[6-(3,5-dimethyl-pyrazol-1-yl)-pyrazin-2-yl]-amine (Compound 4)

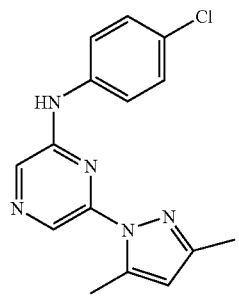 [SMILES: Cc1cc(C)n(-c2cncc(Nc3ccc(Cl)cc3)n2)n1]

Sodium hydride (60% in mineral oil, 161 mg, 4.03 mmol) was added to a suspension of 4-chloroaniline (489 mg, 3.83 mmol) in dimethylsulfoxide (10 mL). The mixture was stirred at 130° C. for 5 minutes. 2-Chloro-6-(3,5-dimethyl-pyrazol-1-yl)-pyrazine was added and the resulting mixture was stirred at 130° C. for 30 minutes. Cooling, followed by addition of water gave a brown precipitate. The brown solid was collected by filtration, re-dissolved in ethyl acetate, washed with brine, dried over sodium sulphate, filtrated and evaporated. The crude product was purified by flash chromatography to give (4-chloro-phenyl)-[6-(3,5-dimethyl-pyrazol-1-yl)-pyrazin-2-yl]-amine (318 mg, 55%) as a brown solid.

Mp.=157-158.9° C. LC-ESI-HRMS of [M+H]+ shows 300.1022 Da. Calc. 300.101598 Da, dev. 2 ppm.

Example 5

(4-Chloro-phenyl)-[6-(6-methyl-pyridin-2-yl)-pyrazin-2-yl]-carbamic acid tert-butyl ester (Intermediate Compound)

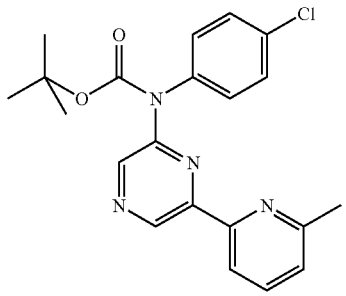 [SMILES: Cc1cccc(-c2cncc(N(C(=O)OC(C)(C)C)c3ccc(Cl)cc3)n2)n1]

Bis(triphenylphosphine)palladium(II) dichloride (54 mg, 0.076 mmol) was dissolved in degassed tetrahydrofuran (5 mL) Diisobutylaluminum hydride (1M in hexanes, 0.15 mL, 0.15 mmol) was added and the mixture was stirred for 15 minutes. 6-Methyl-2-pyridylzinc bromide (0.5 M in tetrahydrofuran, 2.29 mL, 1.15 mmol) and a solution of (4-chlorophenyl)-(6-chloro-pyrazin-2-yl)-carbamic acid tert-butyl ester (260 mg, 0.76 mmol) in tetrahydrofuran (3 mL) was added and the mixture was stirred at room temperature over night. The reaction was quenched with aqueous sodium hydrogen carbonate. The aqueous phase was extracted with ethyl acetate (4×15 mL). The combined organic phases were washed with brine, dried over anhydrous sodium sulphate, filtrated and evaporated. The crude product was purified by column chromatography (ethyl acetate/heptane as eluent) to give (4-chloro-phenyl)-[6-(6-methyl-pyridin-2-yl)-pyrazin-2-yl]-carbamic acid tert-butyl ester (113 mg, 23%) as a yellow solid.

(4-Chloro-phenyl)-[6-(6-methoxy-pyridin-2-yl)-pyrazin-2-yl]-carbamic acid tert-butyl ester (Intermediate Compound)

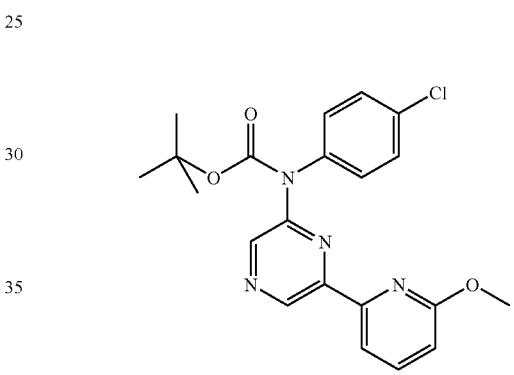

Was prepared according to Example 5 from (4-chlorophenyl)-(6-chloro-pyrazin-2-yl)-carbamic acid tert-butyl ester and 6-methoxy-2-pyridylzinc bromide.

(4-Chloro-phenyl)-(6-pyridin-2-yl-pyrazin-2-yl)-carbamic acid tert-butyl ester (Intermediate Compound)

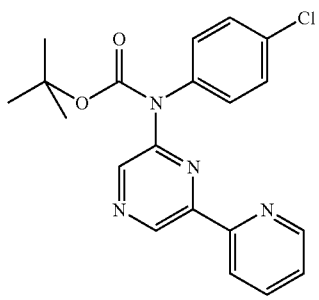 [SMILES: CC(C)(C)OC(=O)N(c1ccc(Cl)cc1)c1cncc(-c2ccccn2)n1]

Was prepared according to Example 5 from (4-chlorophenyl)-(6-chloro-pyrazin-2-yl)-carbamic acid tert-butyl ester and 2-pyridylzinc bromide.

21

(4-Chloro-phenyl)-(6-thiazol-2-yl-pyrazin-2-yl)-carbamic acid tert-butyl ester (Intermediate Compound)

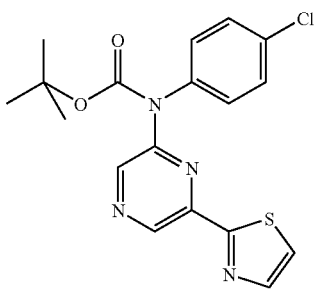 [SMILES: CC(C)(C)OC(=O)N(c1ccc(Cl)cc1)c1cncc(-c2nccs2)n1]

Was prepared according to Example 5 from (4-chloro-phenyl)-(6-chloro-pyrazin-2-yl)-carbamic acid tert-butyl ester and 2-thiazolylzinc bromide.

Example 6

(4-Chloro-phenyl)-(6-pyrimidin-2-yl-pyrazin-2-yl)-carbamic acid tert-butyl ester (Intermediate Compound)

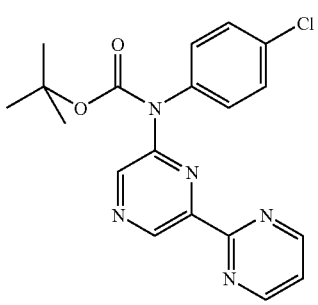 [SMILES: CC(C)(C)OC(=O)N(c1ccc(Cl)cc1)c1cncc(-c2ncccn2)n1]

Bis(triphenylphosphine)palladium(II) dichloride (95 mg, 0.13 mmol) and 2-(tributylstannyl)-pyrimidine (493 mg, 1.34 mmol) were added to a degassed solution of (4-chloro-phenyl)-(6-chloro-pyrazin-2-yl)-carbamic acid tent-butyl ester (500 mg, 1.47 mmol) and lithium chloride (170 mg, 4.00 mmol) in toluene (5 mL) and the mixture was heated to reflux over night. The reaction was quenched with aqueous sodium hydrogen carbonate and brine. The aqueous phase was extracted with ethyl acetate (4×15 mL). The combined organic phases were washed with brine, dried over anhydrous sodium sulphate, filtrated and evaporated. The crude product was purified by column chromatography (ethyl acetate/heptane as eluent) to give (4-chloro-phenyl)-(6-pyrimidin-2-yl-pyrazin-2-yl)-carbamic acid tert-butyl ester (53 mg, 10%) as a white solid.

22

[2,2']Bipyrazinyl-6-yl-(4-chloro-phenyl)-carbamic acid tert-butyl ester (Intermediate Compound)

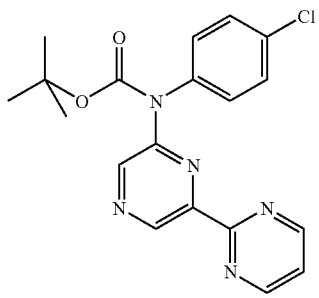 [SMILES: CC(C)(C)OC(=O)N(c1ccc(Cl)cc1)c1cncc(-c2ncccn2)n1]

Was prepared according to Example 6 from (4-chloro-phenyl)-(6-chloro-pyrazin-2-yl)-carbamic acid tert-butyl ester and 2-tributylstannylpyrazine.

Example 7

(4-Chloro-phenyl)-[6-(2H-pyrazol-3-yl)-pyrazin-2-yl]-carbamic acid tert-butyl ester (Intermediate Compound)

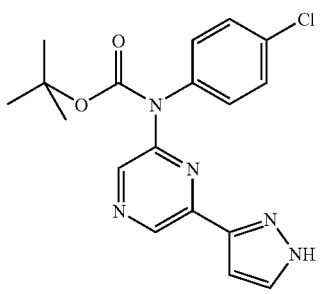 [SMILES: CC(C)(C)OC(=O)N(c1ccc(Cl)cc1)c1cncc(-c2cc[nH]n2)n1]

(4-Chloro-phenyl)-(6-chloro-pyrazin-2-yl)-carbamic acid tert-butyl ester (350 mg, 1.03 mmol), 1H-pyrazole-3-boronic acid (128 mg, 1.13 mmol) and sodium carbonate (218 mg, 2.06 mmol) in water (1 mL) and ethanol (4 mL) were degassed with argon for 30 minutes before tetrakis(triphenylphosphine)palladium(0) (59 mg, 0.051 mmol) was added. The reaction mixture was heated to reflux over night. Water was added and the mixture was concentrated in vacuo. The remaining aqueous phase was extracted with ethyl acetate (3×50 mL) and the combined organic phases were washed with brine, dried over sodium sulphate, filtrated and evaporated. The crude product was purified by column chromatography (ethyl acetate/heptane as eluent) to give (4-chloro-phenyl)-[6-(2H-pyrazol-3-yl)-pyrazin-2-yl]-carbamic acid tert-butyl ester (100 mg, 26%) as a colourless solid.

Example 8

(4-Chloro-phenyl)-[6-(6-methyl-pyridin-2-yl)-pyrazin-2-yl]-amine (Compound 8.1)

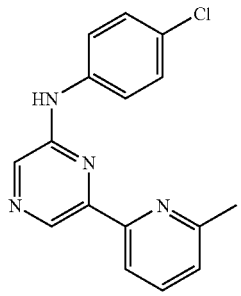 [SMILES: Cc1cccc(-c2cncc(Nc3ccc(Cl)cc3)n2)n1]

Trifluoroacetic acid (1.0 mL, 13.4 mmol) in dichloromethane (3 mL) was added to an ice cooled solution of (4-chloro-phenyl)-[6-(6-methyl-pyridin-2-yl)-pyrazin-2-yl]-carbamic acid tert-butyl ester (70 mg, 0.18 mmol) in dichloromethane (4 mL) and stirred for 2.5 hour at room temperature. The reaction mixture was cooled on an ice bath and aqueous ammonium hydroxide was added followed by evaporation of dichloromethane. The formed precipitate was filtered off. The crude product was purified by flash chromatography (ethyl acetate/heptane as eluent) to give (4-chloro-phenyl)-[6-(6-methyl-pyridin-2-yl)-pyrazin-2-yl]-amine (51 mg, 98%).

Mp.=186-188° C. LC-ESI-HRMS of [M+H]+ shows 297.0898 Da. Calc. 297.090699 Da, dev. −3 ppm.

(4-Chloro-phenyl)-[6-(6-methoxy-pyridin-2-yl)-pyrazin-2-yl]-amine (Compound 8.2)

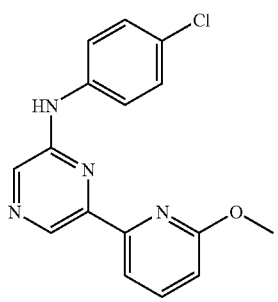 [SMILES: COc1cccc(-c2cncc(Nc3ccc(Cl)cc3)n2)n1]

Was prepared according to Example 8 from (4-chloro-phenyl)-[6-(6-methoxy-pyridin-2-yl)-pyrazin-2-yl]-carbamic acid tert-butyl ester.

Mp.=216-219° C. LC-ESI-HRMS of [M+H]+ shows 313.0848 Da. Calc. 313.085614 Da, dev. −2.6 ppm.

(4-Chloro-phenyl)-(6-pyridin-2-yl-pyrazin-2-yl)-amine (Compound 8.3)

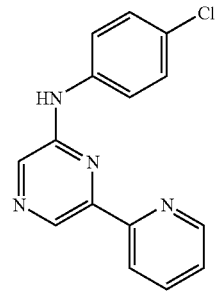 [SMILES: Clc1ccc(Nc2cncc(-c3ccccn3)n2)cc1]

Was prepared according to Example 8 from (4-chloro-phenyl)-(6-pyridin-2-yl-pyrazin-2-yl)-carbamic acid tert-butyl ester.

Mp.=206-207° C. LC-ESI-HRMS of [M+H]+ shows 283.0751 Da. Calc. 283.075049 Da, dev. 0.2 ppm.

(4-Chloro-phenyl)-(6-thiazol-2-yl-pyrazin-2-yl)-amine (Compound 8.4)

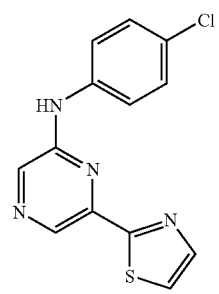 [SMILES: Clc1ccc(Nc2cncc(-c3nccs3)n2)cc1]

Was prepared according to Example 8 from (4-chloro-phenyl)-(6-thiazol-2-yl-pyrazin-2-yl)-carbamic acid tert-butyl ester.

Mp.=167-169° C.

(4-Chloro-phenyl)-(6-pyrimidin-2-yl-pyrazin-2-yl)-amine (Compound 8.5)

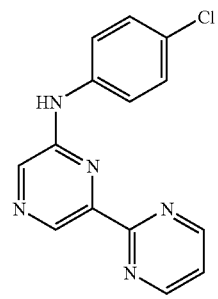 [SMILES: Clc1ccc(Nc2cncc(-c3ncccn3)n2)cc1]

Was prepared according to Example 8 from (4-chloro-phenyl)-(6-pyrimidin-2-yl-pyrazin-2-yl)-carbamic acid tert-butyl ester.

Mp.=212-215° C. LC-ESI-HRMS of [M+H]+ shows 284.0689 Da. Calc. 284.070298 Da, dev. −4.9 ppm.

[2,2']Bipyrazinyl-6-yl-(4-chloro-phenyl)-amine (Compound 8.6)

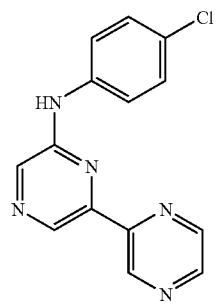 [SMILES: Clc1ccc(Nc2cncc(-c3cnccn3)n2)cc1]

Was prepared according to Example 8 from [2,2']bipyrazinyl-6-yl-(4-chloro-phenyl)-carbamic acid tert-butyl ester.

Mp.=200-201° C. LC-ESI-HRMS of [M+H]+ shows 284.069 Da. Calc. 284.070298 Da, dev. −4.6 ppm.

(4-Chloro-phenyl)-[6-(1H-pyrazol-3-yl)-pyrazin-2-yl]-amine (Compound 8.7)

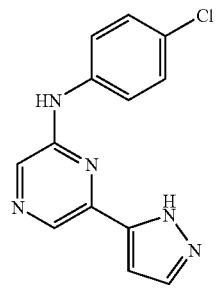 [SMILES: Clc1ccc(Nc2cncc(-c3ccn[nH]3)n2)cc1]

Was prepared according to Example 8 from (4-chloro-phenyl)-[6-(2H-pyrazol-3-yl)-pyrazin-2-yl]-carbamic acid tert-butyl ester.

Mp.=177-180° C. LC-ESI-HRMS of [M+H]+ shows 272.069 Da. Calc. 272.070298 Da, dev. −4.8 ppm.

(4-Chloro-phenyl)-[6-(3-methoxy-pyridin-2-yl)-pyrazin-2-yl]-amine (Compound 8.8)

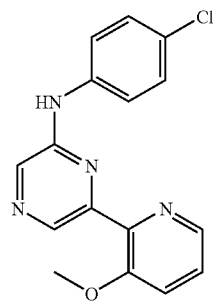 [SMILES: COc1cccnc1-c1cncc(Nc2ccc(Cl)cc2)n1]

Was prepared according to Example 8 from (4-chloro-phenyl)-[6-(3-methoxy-pyridin-2-yl)-pyrazin-2-yl]-carbamic acid tert-butyl ester.

Mp.154-156° C. LC-ESI-HRMS of [M+H]+ shows 313.0843 Da. Calc. 313.085614 Da, dev. −4.2 ppm.

4-Chloro-phenyl)-[6-(1-methyl-1H-benzoimidazol-2-yl)-pyrazin-2-yl]-amine (Compound 8.9)

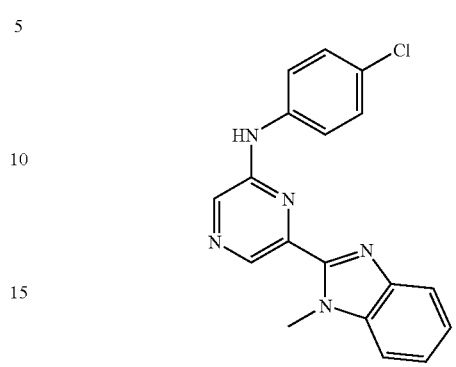

Was prepared according to Example 8 from (4-chloro-phenyl)-[6-(1-methyl-1H-benzoimidazol-2-yl)-pyrazin-2-yl]-carbamic acid tert-butyl ester.

Mp.=220-222° C. LC-ESI-HRMS of [M+H]+ shows 336.1016 Da. Calc. 336.101598 Da, dev. 0 ppm Example 9

3-Chloro-5-(3,5-dimethyl-pyrazol-1-yl)-pyrazine-2-carbaldehyde; and 5-Chloro-3-(3,5-dimethyl-pyrazol-1-yl)-pyrazine-2-carbaldehyde (Intermediate Compounds)

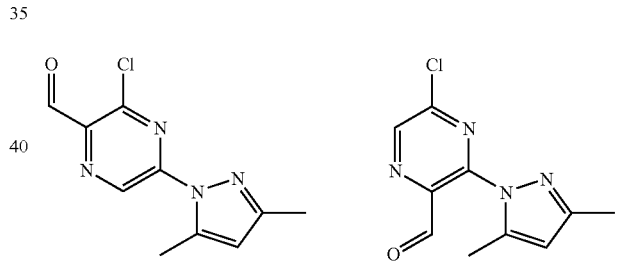

2,2,6,6-Tetramethylpiperidine (20.3 mL, 117 mmol) was added to a solution of n-butyllithium (2.5 M in hexanes, 46 mL, 115 mmol) in dry tetrahydrofuran (1.1 L) at −30° C. The mixture was warmed to room temperature and stirred for 15 minutes. After cooling to −78° C. 2-chloro-6-(3,5-dimethyl-pyrazol-1-yl)-pyrazine (20 g, 96 mmol) in dry tetrahydrofuran (15 mL) was added and the mixture was stirred at −78° C. for 1 h. Ethylformate (12 mL, 143 mmol) was added and the mixture stirred for an additional 2 hours at −78° C. The reaction was quenched with aqueous ammonium chloride, warmed to room temperature and diluted with ethyl acetate. The layers were separated and the aqueous phase was extracted with ethyl acetate. The combined organic layers were washed with brine and dried over sodium sulphate, filtrated and evaporated to give the crude product as a yellow solid. The crude products were purified by flash chromatography (ethyl acetate/heptane as eluent) to give 3-chloro-5-(3,5-dimethyl-pyrazol-1-yl)-pyrazine-2-carbaldehyde (2.9 g, 13%) as a yellow solid and 5-chloro-3-(3,5-dimethyl-pyrazol-1-yl)-pyrazine-2-carbaldehyde (700 mg, 3%) as a yellow solid.

Example 10

3-Chloro-5-(3,5-dimethyl-pyrazol-1-yl)-2-[1,3]-diagonal-2-yl-pyrazine (Intermediate Compound)

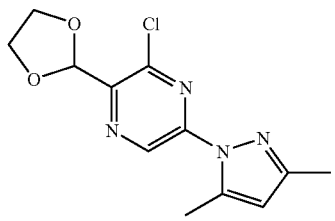 [SMILES: Cc1cc(C)n(-c2cnc(C3OCCO3)c(Cl)n2)n1]

Ethylene glycol (171 μL, 3.17 mmol) and p-toluenesulfonic acid monohydrate (24 mg, 0.13 mmol) was added to a solution of 3-chloro-5-(3,5-dimethyl-pyrazol-1-yl)-pyrazine-2-carbaldehyde (300 mg, 1.27 mmol) in dry toluene (40 mL). The reaction was heated to reflux in a Dean-Stark reaction system overnight. After cooling to room temperature aqueous sodium hydrogen carbonate was added and the layers were separated. The aqueous phase was extracted with ethyl acetate and the combined organic layers were washed with brine, dried over sodium sulphate, filtrated and evaporated to give 3-chloro-5-(3,5-dimethyl-pyrazol-1-yl)-2-[1,3]diagonal-2-yl-pyrazine (343 mg, 96%) as the crude product. This product was used without further purification.

5-Chloro-3-(3,5-dimethyl-pyrazol-1-yl)-[1,3]diagonal-2-yl-pyrazine (Intermediate Compound)

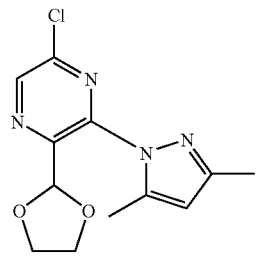

Was prepared according to Example 10 from 5-chloro-3-(3,5-dimethyl-pyrazol-1-yl)-pyrazine-2-carbaldehyde and ethylene glycol.

Example 11

(4-Chloro-phenyl)-[6-(3,5-dimethyl-pyrazol-1-yl)-3-[1,3]-diagonal-2-yl-pyrazin-2-yl]-amine (Intermediate Compound)

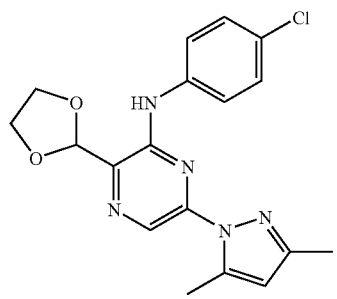 [SMILES: Cc1cc(C)n(-c2cnc(C3OCCO3)c(Nc3ccc(Cl)cc3)n2)n1]

A mixture of 3-chloro-5-(3,5-dimethyl-pyrazol-1-yl)-2-[1,3]diagonal-2-yl-pyrazine (266 mg, 0.95 mmol), 4-chloroaniline (169 mg, 1.33 mmol) and cesium carbonate (624 mg, 1.90 mmol) in dry dioxane (10 mL) was degassed with argon for 15 minutes. Tris(dibenzylideneacetone)dipalladium (0) (22 mg, 0.02 mmol) and 1,1'-bis(diphenylphosphino)ferrocene (43 mg, 0.08 mmol) were added followed by degassing for 5 minutes and stirring at 120° C. overnight. The reaction mixture was allowed to cool down, diluted with dichloromethane and filtrated through celite. The filter cake was washed with dichloromethane and the filtrate was concentrated in vacuo. The crude product was purified by flash chromatography (ethyl acetate/heptane as eluent) to give (4-chloro-phenyl)-[6-(3,5-dimethyl-pyrazol-1-yl)-3-[1,3]diagonal-2-yl-pyrazin-2-yl]-amine (285 mg, 81%) as a off-white solid.

4-Chloro-phenyl)-[6-(3,5-dimethyl-pyrazol-1-yl)-5-[1,3]diagonal-2-yl-pyrazin-2-yl]-amine (Intermediate Compound)

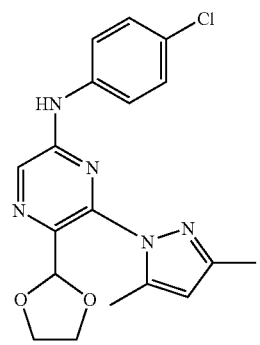 [SMILES: Cc1cc(C)n(-c2nc(Nc3ccc(Cl)cc3)cnc2C2OCCO2)n1]

Was prepared according to Example 11 from 5-chloro-3-(3,5-dimethyl-pyrazol-1-yl)-2-[1,3]diagonal-2-yl-pyrazine and 4-chloroaniline.

Example 12

3-(4-Chloro-phenylamino)-5-(3,5-dimethyl-pyrazol-1-yl)-pyrazine-2-carbaldehyde (Intermediate Compound)

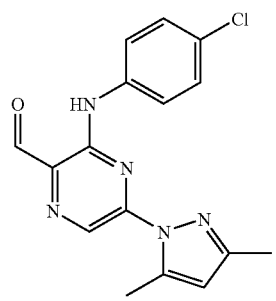 [SMILES: Cc1cc(C)n(-c2cnc(C=O)c(Nc3ccc(Cl)cc3)n2)n1]

Aqueous hydrochloric acid (1M, 860 μL, 0.86 mmol) was added to a solution of (4-chloro-phenyl)-[6-(3,5-dimethyl-pyrazol-1-yl)-3-[1,3]diagonal-2-yl-pyrazin-2-yl]-amine (80 mg, 0.22 mmol) in acetone (5 mL) and stirred for 30 minutes at room temperature. The reaction mixture was concentrated in vacuo and co-evaporated with acetone, ethyl acetate and diethyl ether to give 3-(4-chloro-phenylamino)-5-(3,5-dimethyl-pyrazol-1-yl)-pyrazine-2-carbaldehyde (80 mg, 100%).

5-(4-Chloro-phenylamino)-3-(3,5-dimethyl-pyrazol-1-yl)-pyrazine-2-carbaldehyde (Intermediate Compound)

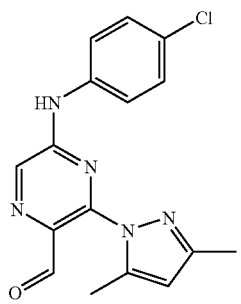 [SMILES: Cc1cc(C)n(-c2nc(Nc3ccc(Cl)cc3)cnc2C=O)n1]

Was prepared according to Example 12 from (4-chloro-phenyl)-[6-(3,5-dimethyl-pyrazol-1-yl)-5-[1,3]diagonal-2-yl-pyrazin-2-yl]-amine.

Example 13

[3-(4-Chloro-phenylamino)-5-(3,5-dimethyl-pyrazol-1-yl)-pyrazin-2-yl]-methanol (Intermediate Compound)

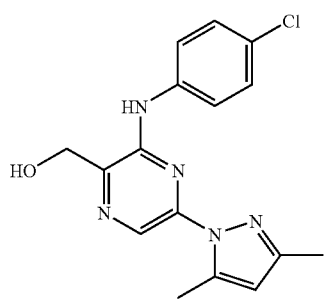 [SMILES: Cc1cc(C)n(-c2cnc(CO)c(Nc3ccc(Cl)cc3)n2)n1]

Sodium borohydride (25 mg, 0.66 mmol) was added to an ice cooled solution of 3-(4-chloro-phenylamino)-5-(3,5-dimethyl-pyrazol-1-yl)-pyrazine-2-carbaldehyde (80 mg, 0.22 mmol) in methanol (5 mL) and stirred at room temperature for 30 minutes. The reaction was quenched with aqueous sodium hydrogen carbonate and diluted with ethyl acetate. The organic solvents were evaporated and the remaining aqueous phase was extracted with ethyl acetate (3×20 mL). The combined organic phases were washed with brine, dried over sodium sulphate, filtrated and evaporated to give [3-(4-chloro-phenylamino)-5-(3,5-dimethyl-pyrazol-1-yl)-pyrazin-2-yl]-methanol (58 mg, 80%) as the crude product.

[5-(4-Chloro-phenylamino)-3-(3,5-dimethyl-pyrazol-1-yl)-pyrazin-2-yl]-methanol (Intermediate Compound)

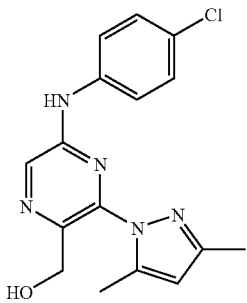 [SMILES: Cc1cc(C)n(-c2nc(Nc3ccc(Cl)cc3)cnc2CO)n1]

Was prepared according to Example 13 from 5-(4-chlorophenylamino)-3-(3,5-dimethyl-pyrazol-1-yl)-pyrazine-2-carbaldehyde.

[3-Chloro-5-(3,5-dimethyl-pyrazol-1-yl)-pyrazin-2-yl]-methanol (Intermediate Compound)

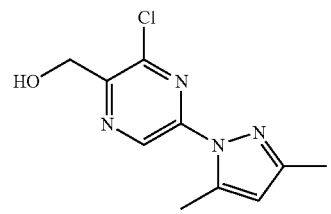 [SMILES: Cc1cc(C)n(-c2cnc(CO)c(Cl)n2)n1]

Was prepared according to Example 13 from 3-chloro-5-(3,5-dimethyl-pyrazol-1-yl)-pyrazine-2-carbaldehyde.

Example 14

(4-Chloro-phenyl)-[3-dimethylaminomethyl-6-(3,5-dimethyl-pyrazol-1-yl)-pyrazin-2-yl]-amine (Compound 14.1)

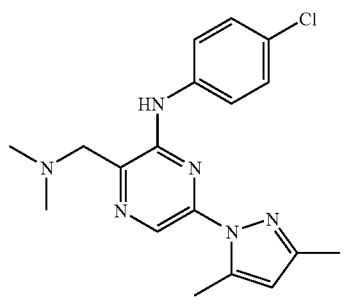

Methanesulfonyl chloride (274, 0.35 mmol) was added to a solution of [3-(4-chloro-phenylamino)-5-(3,5-dimethyl-pyrazol-1-yl)-pyrazin-2-yl]-methanol (58 mg, 0.18 mmol) and triethylamine (75 μL, 0.53 mmol) in dichloromethane (5 mL) and tetrahydrofuran (1 mL) and stirred for 15 minutes. Dimethylamine (2M in tetrahydrofuran, 1.32 mL, 2.64 mmol) was added and the solution was stirred overnight.

Water and ethyl acetate were added and the organic solvents were evaporated in vacuo. The remaining aqueous phase was extracted with ethyl acetate. The combined organic phases were washed with brine, dried over sodium sulphate, filtrated and evaporated to give the crude product as a brown oil. Purification by flash chromatography (dichloromethane/methanol as eluent) gave (4-chloro-phenyl)-[3-dimethylaminomethyl-6-(3,5-dimethyl-pyrazol-1-yl)-pyrazin-2-yl]-amine (52 mg, 82%) as a brown solid.

Mp.=112-114° C. LC-ESI-HRMS of [M+H]+ shows 357.1613 Da. Calc. 357.159447 Da, dev. 5.2 ppm.

4-Chloro-phenyl)-[6-(3,5-dimethyl-pyrazol-1-yl)-3-methylaminomethyl-pyrazin-2-yl]-amine (Compound 14.2)

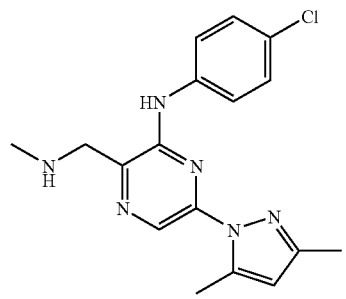

Was prepared according to Example 14 from [3-(4-chlorophenylamino)-5-(3,5-dimethyl-pyrazol-1-yl)-pyrazin-2-yl]-methanol and methylamine.

Mp.=90-93° C. LC-ESI-HRMS of [M+H]+ shows 343.1425 Da. Calc. 343.143797 Da, dev. −3.8 ppm.

4-Chloro-phenyl)-[5-dimethylaminomethyl-6-(3,5-dimethyl-pyrazol-1-yl)-pyrazin-2-yl]-amine (Compound 14.3)

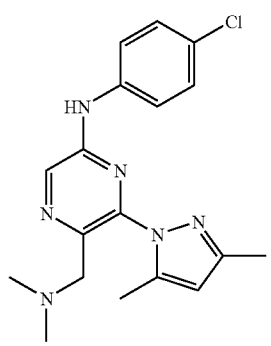

Was prepared according to Example 14 from [5-(4-chlorophenylamino)-3-(3,5-dimethyl-pyrazol-1-yl)-pyrazin-2-yl]methanol and dimethylamine.

Mp. 142-146° C. LC-ESI-HRMS of [M+H]+ shows 357.1613 Da. Calc. 357.159447 Da, dev. 5.2 ppm 4-Chloro-phenyl)-[6-(3,5-dimethyl-pyrazol-1-yl)-5-methylaminomethyl-pyrazin-2-yl]-amine (Compound 14.4)

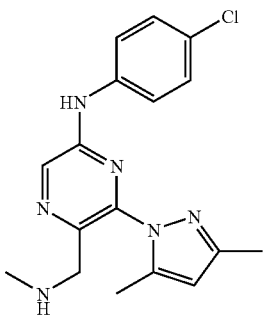

Was prepared according to Example 14 from [5-(4-chlorophenylamino)-3-(3,5-dimethyl-pyrazol-1-yl)-pyrazin-2-yl]methanol and methylamine.

Mp. 179-182° C. LC-ESI-HRMS of [M+H]+ shows 343.1427 Da. Calc. 343.143797 Da, dev. −3.2 ppm Example 15

3-Chloro-5-(3,5-dimethyl-pyrazol-1-yl)-2-methoxymethyl-pyrazine (Intermediate Compound)

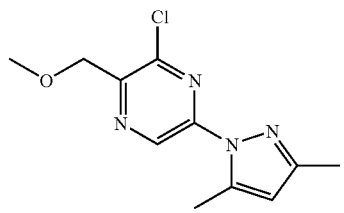

Sodium hydride (60% in mineral oil, 18 mg, 0.45 mmol) was added to a solution of [3-chloro-5-(3,5-dimethyl-pyrazol-1-yl)-pyrazin-2-yl]methanol (102 mg, 0.43 mmol) in dimethyl sulfoxide (4 mL) and stirred for 15 minutes. Iodomethane (29 μL, 0.74 mmol) was added and the mixture was stirred at room temperature for 30 minutes and at 50° C. for 30 minutes. Sodium hydride (60% in mineral oil, 50 mg) and iodomethane (200 μL) was added and the mixture was stirred at 50° C. for 30 minutes. After cooling down water was added and a brown solid formed. Filtration followed by redissolvation in ethyl acetate, wash with brine, drying over sodium sulphate, filtration and evaporation gave the crude material. Flash chromatography (ethyl acetate/heptane as eluent) gave 3-chloro-5-(3,5-dimethyl-pyrazol-1-yl)-2-methoxymethyl-pyrazine (34 mg, 32%) as a yellow solid.

Example 16

(4-Chloro-phenyl)-[6-(3,5-dimethyl-pyrazol-1-yl)-3-methoxymethyl-pyrazin-2-yl]-amine (Compound 16.1)

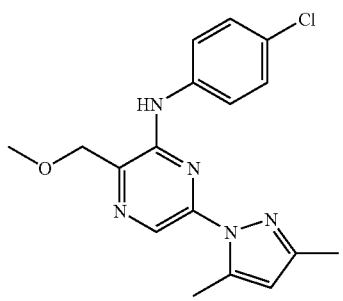

A mixture of 3-chloro-5-(3,5-dimethyl-pyrazol-1-yl)-2-methoxymethyl-pyrazine (34 mg, 0.12 mmol), 4-chloroaniline (22 mg, 0.17 mmol) and cesium carbonate (80 mg, 0.24 mmol) in dry dioxane (2 mL) was degassed with argon for 15 minutes. Tris(dibenzylideneacetone)dipalladium (0) (3 mg, 0.003 mmol) and 1,1'-bis(diphenyl-phosphino) ferrocene (6 mg, 0.01 mmol) were added followed by degassing for 5 minutes and the reaction mixture was stirred at 120° C. over night. Dichloromethane was added and the solution was filtrated. The filtrate was concentrated in vacuo. Flash chromatography (ethyl acetate/heptane as eluent) gave (4-chloro-phenyl)-[6-(3,5-dimethyl-pyrazol-1-yl)-3-methoxymethyl-pyrazin-2-yl]-amine (33 mg, 80%) as a white solid.

Mp.=105-108° C. LC-ESI-HRMS of [M+H]+ shows 344.1278 Da. Calc. 344.127813 Da, dev. 0 ppm.

Example 17

4-Chloro-phenyl)-[6-(3,5-dimethyl-pyrazol-1-yl)-5-methoxymethyl-pyrazin-2-yl]-amine (Compound 17.1)

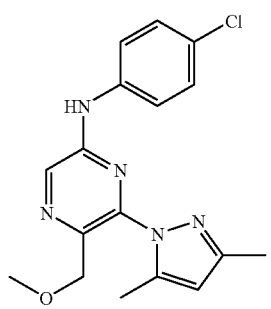

To a solution of [5-(4-chloro-phenylamino)-3-(3,5-dimethyl-pyrazol-1-yl)-pyrazin-2-yl]-methanol (50 mg, 0.15 mmol) and triethyl amine (0.06 mL, 0.45 mmol) in tetrahydrofuran (5 mL) was added methanesulfonyl chloride (0.23 mL, 0.30 mmol) and the solution was stirred for 15 min. Sodium methoxide (30 5 in methanol, 0.85 mL, 4.5 mmol) was added and the mixture was stirred for 1.5 hour. Water (20 mL) and brine (30 mL) was added and the qquosus phase was extracted with ethyl acetate. The combined organic phases were dried over magnesium sulphate, filtrated and concentrated in vacuo. The crude product was purified by flash chromatography to give (4-chloro-phenyl)-[6-(3,5-dimethyl-pyrazol-1-yl)-5-methoxymethyl-pyrazin-2-yl]-amine (5 mg, 8%) as an orange solid. Mp. 147-151° C. LC-ESI-HRMS of [M+Na]+ shows 366.1087 Da. Calc. 366.109788 Da, dev. −3 ppm

Example 18

(4-Chloro-phenyl)-[6-(3-methoxy-pyridin-2-yl)-pyrazin-2-yl]-carbamic acid tert-butyl ester (Intermediate Compound)

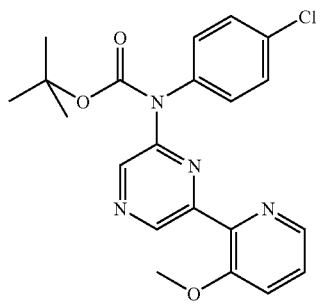 [SMILES: COc1cccnc1-c1cncc(N(C(=O)OC(C)(C)C)c2ccc(Cl)cc2)n1]

Mixture A: tert-Butyllithium (1.5 M in pentane, 1.8 mL) was added slowly to a solution of 2-bromo-3-methoxypyridine (249 mg, 1.32 mmol) in dry tetrahydrofuran (2 mL) at −78° C. and the resulting mixture was stirred for 15 minutes. Zinc chloride (1M in diethyl ether, 1.76 mL, 2.65 mmol) was added and stirring was continued 30 minutes at room temperature.

Mixture B: At the same time in another flask (4-chloro-phenyl)-(6-chloro -pyrazin-2-yl)-carbamic acid tert-butyl ester (300 mg, 0.88 mmol) was added to a degassed solution of bis(triphenylphosphine)palladium(II) dichloride (125 mg, 0.18 mmol) and diisobutylaluminum hydride (1M in hexanes, 0.53 mL) in tetrahydrofuran (2 mL) and the resulting mixture was stirred for 10 minutes at room temperature.

Mixture B was added to mixture A and the resulting reaction mixture was heated to reflux overnight.

The reaction was quenched with water and the organic solvents were evaporated in vacuo. The aqueous phase was extracted with ethyl acetate (3×20 mL). The combined organic phases were washed with brine, dried over sodium sulphate, filtrated and evaporated. The crude product was purified by flash chromatography (ethyl acetate/heptane as eluent) to give (4-chloro-phenyl)-[6-(3-methoxy-pyridin-2-yl)-pyrazin-2-yl]-carbamic acid tert-butyl ester (40 mg, 11%) as an orange solid.

Example 19

4-Chloro-phenyl)-[6-(1-methyl-1H-benzoimidazol-2-yl)-pyrazin-2-yl]-carbamic acid tert-butyl ester (Intermediate Compound)

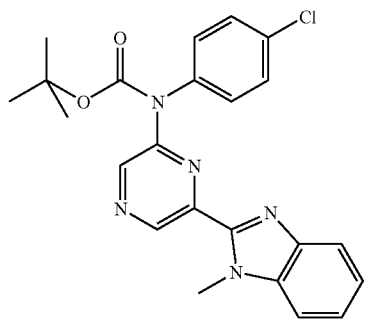 [SMILES: Cn1c(-c2cncc(N(C(=O)OC(C)(C)C)c3ccc(Cl)cc3)n2)nc2ccccc21]

Mixture A: tert-Butyllithium (1.5 M in pentanes, 1.76 mL, 2.64 mmol) was added slowly to a solution of 1-methylbenzimidazole (174 mg, 1.32 mmol) in tetrahydrofuran (2 mL) at −78° C. After stirring for 15 minutes at −78° C. zinc chloride (1M in diethylether, 1.45 mL) was added and stirring was continued for 30 minutes at room temperature.

Mixture B: (4-Chloro-phenyl)-(6-chloro-pyrazin-2-yl)-carbamic acid tert-butyl ester (300 mg, 0.88 mmol) was added to a degassed solution of bis(triphenylphosphine)palladium (II) dichloride (125 mg, 0.17 mmol) and diisobutylaluminum hydride (1M in hexanes, 0.53 mL) in tetrahydrofuran (2 mL). The resulting mixture was stirred for 10 minutes at room temperature.

Mixture B was transferred to mixture A and the resulting mixture was heated at reflux overnight. The reaction was quenched with water diluted with ethyl acetate. The organic solvents were evaporated in vacuo. The aqueous phase was extracted with ethyl acetate (3×30 mL). The combined organic phases were washed with brine and dried over sodium sulphate, filtrated, concentrated in vacuo to give the crude product.

Flash chromatography (ethyl acetate/heptane as eluent) gave (4-chloro-phenyl)-[6-(1-methyl-1H-benzoimidazol-2-yl)-pyrazin-2-yl]-carbamic acid tert-butyl ester (91 mg, 24%) as a yellow solid.

Example 20

3-(4-Chloro-phenylamino)-5-(3,5-dimethyl-pyrazol-1-yl)-pyrazine-2-carbaldehyde oxime (Compound 20.1)

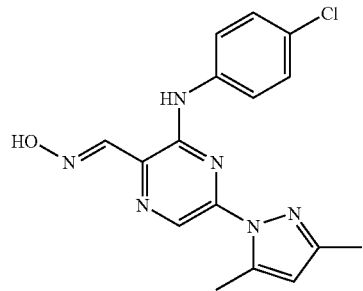 [SMILES: Cc1cc(C)n(-c2cnc(/C=N/O)c(Nc3ccc(Cl)cc3)n2)n1]

3-(4-Chloro-phenylamino)-5-(3,5-dimethyl-pyrazol-1-yl)-pyrazine-2-carbaldehyde (100 mg, 0.27 mmol) was dissolved in ethanol (99%, 10 mL) and hydroxylamine, hydrochloride (20 mg, 0.27 mmol) was added. The mixture was heated to reflux for 3 hours and concentrated in vacuo. Ethyl acetate (30 mL) and aqeuous sodium carbonate (20 mL) were added and stirred for 15 minutes. The layers were separated and the organic phase was washed with brine, dried over sodium sulphate, filtrated and concentrated in vacuo to give 3-(4-chloro-phenylamino)-5-(3,5-dimethyl-pyrazol-1-yl)-pyrazine-2-carbaldehyde oxime (71 mg, 76%) as an orange solid.

Mp. 228-231° C.

LC-ESI-HRMS of [M+H]+ shows 343.1084 Da. Calc. 343.107412 Da, dev. 2.9 ppm 5-(4-Chloro-phenylamino)-3-(3,5-dimethyl-pyrazol-1-yl)-pyrazine-2-carbaldehyde oxime

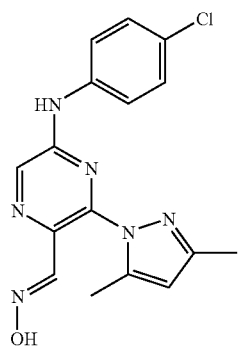 [SMILES: Cc1cc(C)n(-c2nc(Nc3ccc(Cl)cc3)cnc2/C=N/O)n1]

Was prepared according to example 20 from 5-(4-chloro-phenylamino)-3-(3,5-dimethyl-pyrazol-1-yl)-pyrazine-2-carbaldehyde and hydroxylamine, hydrochloride.

Example 21

[3-Aminomethyl-6-(3,5-dimethyl-pyrazol-1-yl)-pyrazin-2-yl]-(4-chloro-phenyl)-amine (Compound 21.1)

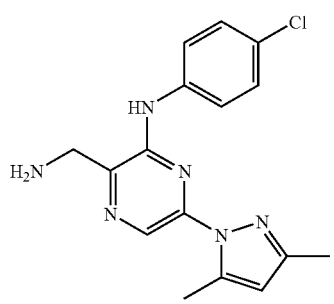 [SMILES: Cc1cc(C)n(-c2cnc(CN)c(Nc3ccc(Cl)cc3)n2)n1]

Raney nickel (50% slurry in water, 1 mL) was added to a solution of 3-(4-chloro-phenylamino)-5-(3,5-dimethyl-pyrazol-1-yl)-pyrazine-2-carbaldehyde oxime (60 mg, 0.17 mmol) in ethanol (99%, 6 mL). The reaction mixture was stirred under a hydrogen atmosphere for one hour. Methanol was added followed by filtration and evaporation. The crude product was purified by flash chromatography (dichloromethane/methanol as eluent) to give [3-aminomethyl-6-(3,5-dimethyl-pyrazol-1-yl)-pyrazin-2-yl]-(4-chloro-phenyl)-amine (16 mg, 28%) as a white solid. Mp.=156-160° C.

[5-Aminomethyl-6-(3,5-dimethyl-pyrazol-1-yl)-pyrazin-2-yl]-(4-chloro-phenyl)-amine (Compound 21.2)

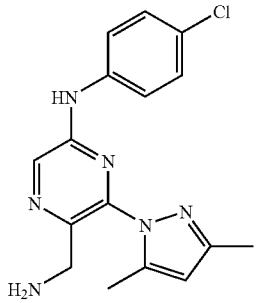 [SMILES: Cc1cc(C)n(-c2nc(Nc3ccc(Cl)cc3)cnc2CN)n1]

Was prepared according to example 21 from 5-(4-chloro-phenylamino)-3-(3,5-dimethyl-pyrazol-1-yl)-pyrazine-2-carbaldehyde oxime. Mp.=173-176° C. LC-ESI-HRMS of [M+H]+ shows 329.1294 Da. Calc. 329.128147 Da, dev. 3.8 ppm

Example 22

N-[3-(4-Chloro-phenylamino)-5-(3,5-dimethyl-pyrazol-1-yl)-pyrazin-2-ylmethyl]-acetamide (Compound 22.1)

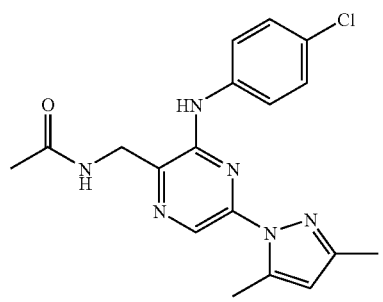 [SMILES: CC(=O)NCc1ncc(-n2nc(C)cc2C)nc1Nc1ccc(Cl)cc1]

[3-Aminomethyl-6-(3,5-dimethyl-pyrazol-1-yl)-pyrazin-2-yl]-(4-chloro-phenyl)-amine (40 mg, 0.12 mmol), triethylamine (19 µL, 0.13 mmol) and dichloromethane (2 mL) was cooled on an ice bath. Acetic anhydride (12 µM, 0.12 mmol) was added and the mixture was stirred for 45 min. Aqueous sodium hydrogen carbonate was added and the aqueous phase was extracted with ethyl acetate (3×). The combined organic phases were dried over sodium sulphate, filtrated and concentrated in vacuo. The crude product was purified by flash chromatography (dichloromethane/methanol as eluent) to give N-[3-(4-chloro-phenylamino)-5-(3,5-dimethyl -pyrazol-1-yl)-pyrazin-2-ylmethyl]-acetamide (29 mg, 64%) as a white solid. Mp. 228-230° C. LC-ESI-HRMS of [M+H]+ shows 371.1404 Da. Calc. 371.138712 Da, dev. 4.5 ppm N-1-[5-(4-Chloro-phenylamino)-3-(3,5-dimethyl-pyrazol-1-O-pyrazin-2-ylmethyl]-acetamide (Compound 22.2)

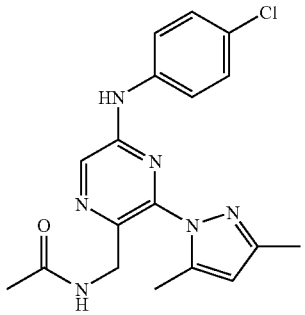 [SMILES: CC(=O)NCc1ncc(Nc2ccc(Cl)cc2)nc1-n1nc(C)cc1C]

Was prepared according to example 22 [5-aminomethyl-6-(3,5-dimethyl-pyrazol-1-yl)-pyrazin-2-yl]-(4-chloro-phenyl)-amine and acetic anhydride.

Mp. 197-199° C.

Example 23

(3,5-Dibromo-pyrazin-2-yl)-carbamic acid tert-butyl ester

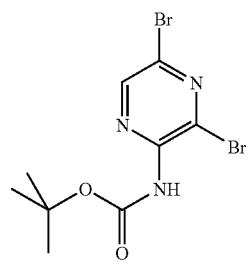 [SMILES: CC(C)(C)OC(=O)Nc1ncc(Br)nc1Br]

Sodium hydride (60% in mineral oil, 223 mg, 5.5 mmol) was added to a solution of 2-amino-3,5-dibromopyrazine (484 mg, 1.8 mmol) in 1,2-dimethoxy-ethane (10 mL) and the reaction mixture was stirred for 30 min. at room temperature. Di-tert-butyl dicarbonate (450 mg, 2.0 mmol) was added and the mixture was stirred at room temperature for 30 min. Water and brine were added and the aqueous phase was extracted with ethyl acetate (3×). The combined organic phases were washed with brine, dried over sodium sulphate, filtrated and concentrated in vacuo to give (3,5-dibromo-pyrazin-2-yl)-carbamic acid tert-butyl ester as the crude product.

Example 24

(5-Bromo-3-hydrazino-pyrazin-2-yl)-carbamic acid tert-butyl ester

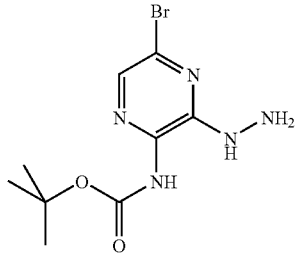 [SMILES: CC(C)(C)OC(=O)Nc1ncc(Br)nc1NN]

(3,5-Dibromo-pyrazin-2-yl)-carbamic acid tert-butyl ester (600 mg, 1.7 mmol) was dissolved in dioxane (10 mL) and cooled on an ice bath. Hydrazine monohydrate (3 mL, 61.7 mmol) was added and the mixture was stirred at room temperature for 2 hours. The reaction mixture was concentrated in vacuo and the remaining residue was re-dissolved in a mixture of ethylacetate, water and brine. The phases were separated and the aqeuous phase was extracted with ethyl acetate (3×30 mL). The combined organic phases were washed with brine, dried over sodium sulphate, filtrated and concentrated in vacuo to give (5-bromo-3-hydrazino-pyrazin-2-yl)-carbamic acid tert-butyl ester as the crude product.

Example 25

[5-Bromo-3-(3,5-dimethyl-pyrazol-1-yl)-pyrazin-2-yl]-carbamic acid tert-butyl ester

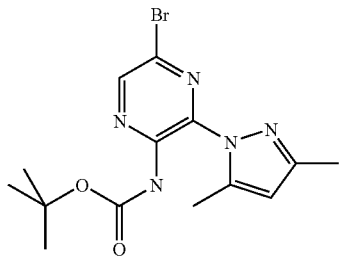 [SMILES: Cc1cc(C)n(-c2nc(Br)cnc2NC(=O)OC(C)(C)C)n1]

(5-Bromo-3-hydrazino-pyrazin-2-yl)-carbamic acid tert-butyl ester (513 mg, 1.6 mmol) and 2,4-pentadione (0.18 mL, 1.7 mmol) in ethanol (25 mL) were heated to reflux for 45 min. The mixture was concentrated in vacuo followed by co-evaporation with ethyl acetate to give [5-bromo-3-(3,5-dimethyl-pyrazol-1-yl)-pyrazin-2-yl]-carbamic acid tert-butyl ester as the crude product.

Example 26

[5-(4-Chloro-phenylamino)-3-(3,5-dimethyl-pyrazol-1-yl)-pyrazin-2-yl]-carbamic acid tert-butyl ester

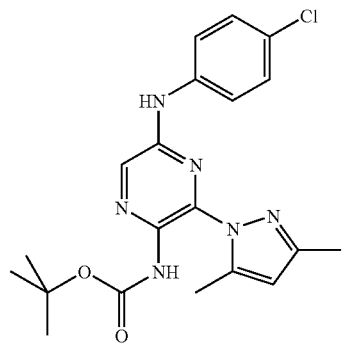 [SMILES: Cc1cc(C)n(-c2nc(Nc3ccc(Cl)cc3)cnc2NC(=O)OC(C)(C)C)n1]

A mixture of give [5-bromo-3-(3,5-dimethyl-pyrazol-1-yl)-pyrazin-2-yl]-carbamic acid tert-butyl ester (511 mg, 1.25 mmol), 4-chloroaniline (223 mg, 1.75 mmol) and cesium carbonate (822 mg, 2.5 mmol) in dioxane (35 mL) was degassed with argon for 15 min. Tris(dibenzylideneaceton) dipalladium (0) 29 mg, 0.03 mmol) and 1,1'-bis(diphenylphosphino)ferrocene (57 mg, 0.1 mmol) were added followed by degassing for 5 min. The reaction mixture was heated to 120° C. for overnight. Ethyl acetate, water and brine were added and the phases were separated. The aqueous phase was extracted with ethyl acetate (5×50 mL). The combined organic phases were washed with brine, dried over sodium sulphate, filtrated and concentrated in vacuo. The crude product purified by flash chromatography (ethyl acetate/heptane as eluent) to give [5-(4-chloro-phenylamino)-3-(3,5-dimethyl-pyrazol-1-yl)-pyrazin-2-yl]-carbamic acid tert-butyl ester (225 mg, 43%) as an yellow solid.

Example 27

5-(4-Chloro-phenylamino)-3-(3,5-dimethyl-pyrazol-1-yl)-pyrazine-2-amine (Compound 27.1)

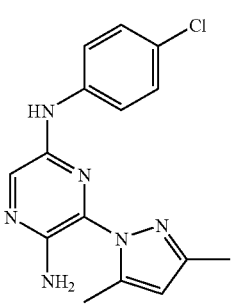 [SMILES: Cc1cc(C)n(-c2nc(Nc3ccc(Cl)cc3)cnc2N)n1]

[5-(4-chloro-phenylamino)-3-(3,5-dimethyl-pyrazol-1-yl)-pyrazin-2-yl]-carbamic acid tert-butyl ester (225 mg, 0.54 mmol) was dissolved in dichloromethane (15 mL) and cooled on an ice bath. Trifluoroacetic acid (2.5 mL, 33 mmol) in dichloromethane (2.5 mL) was added dropwise and stirred for 30 min. The reaction mixture was concentrated in vacuo, re-dissolved in water and alkalised with aqueous ammonia. The aqueous phase was extracted with ethyl acetate (3×30 mL). The combined organic phases were washed with brine, dried over sodium sulphate, filtrated and concentrated in vacuo to give 5-(4-chloro-aniline)-3-(3,5-dimethyl-pyrazol-1-yl)-pyrazine-2,5-diamine (170 mg, 99%) as a brownish solid. Mp. 156-159° C.

LC-ESI-HRMS of [M+H]+ shows 315.1131 Da. Calc. 315.112497 Da, dev. 1.9 ppm 5-(4-Chloro-phenylamino)-3-(3,5-dimethyl-pyrazol-1-yl)-2-ethylamino-pyrazine (compound 27.2)

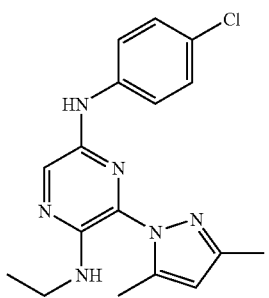 [SMILES: CCNc1ncc(Nc2ccc(Cl)cc2)nc1-n1nc(C)cc1C]

5-(4-Chloro-phenylamino)-3-(3,5-dimethyl-pyrazol-1-yl)-pyrazine-2-amine (84 mg, 1.5 mmol) was dissolved in dichloroethane (4 mL). Acetaldehyde (83 µL, 1.5 mmol) was added and the reaction mixture was stirred for one hour at room temperature. Sodium triaceoxyborohydride (70 mg, 0.3 mmol) was added and the reaction mixture was stirred overnight at room temperature. Aqueous sodium hydrogen carbonate and dichloromethane were added. The phases were separated and the aqueous phase was extracted with dichloromethane (3×20 mL). The combined organic phases were washed with brine, dried over sodium sulphate, filtrated and concentrated in vacuo. The crude product was purified by flash chromatography (ethyl acetate/heptane as eluent) to give 5-(4-chloro-phenylamino)-3-(3,5-dimethyl-pyrazol-1-yl)-2-ethylamino-pyrazine (49 mg, 80%) as a green solid. Mp. 122-124° C. LC-ESI-HRMS of [M+H]+ shows 343.1444 Da. Calc. 343.143797 Da, dev. 1.8 ppm Example 28

Biological Activity

The below examples demonstrates the biological activity of compounds representative of the invention. The ionic current through small-conductance $Ca^{2+}$-activated $K^+$ channels (SK channels, subtype 3) is recorded using the whole-cell configuration of the patch-clamp technique.

HEK293 tissue culture cells expressing hSK3 channels were grown in DMEM (Dulbecco's Modified Eagle Medium) supplemented with 10% FCS (foetal calf serum) at 37° C. in 5% $CO_2$. At 60-80% confluency, cells were harvested by trypsin treatment and seeded on cover slips.

Experiments are carried out on one of several patch-clamp set-ups. Cells plated on coverslips are placed in a 15 µl perfusion chamber (flowrate ~1 ml/min) mounted on an IMT-2 microscope. The microscopes are placed on vibration-free tables in grounded Faraday cages. All experiments are performed at room temperature (20-22° C.). EPC-9 patch-clamp amplifiers (HEKA-electronics, Lambrect, Germany) are connected to Macintosh computers via ITC16 interfaces. Data are stored directly on the hard-disk and analysed by IGOR software (Wavemetrics, Lake Oswega, Oreg., USA).

The whole-cell configuration of the patch-clamp technique is applied. In short: The tip of a borosilicate pipette (resistance 2-4 MΩ) is gently placed on the cell membrane using remote control systems. Light suction results in the formation of a giga seal (pipette resistance increases to more than 1 GΩ) and the cell membrane underneath the pipette is then ruptured by more powerful suction. Cell capacitance is electronically compensated and the resistance between the pipette and the cell interior (the series resistance, Rs) is measured and compensated for. Usually the cell capacitance ranges from 5 to 20 pF (depending on cell size) and the series resistance is in the range 3 to 6 MΩ. Rs- as well as capacitance compensation are updated during the experiments (before each stimulus). All experiments with drifting Rs-values are discharged. Leak-subtractions are not performed.

The extracellular (bath) solution contains (in mM): 154 mM KCl, 0.1 $CaCl_2$, 3 $MgCl_2$, 10 HEPES (pH=7.4 with HCl). The test compound was dissolved 1000 times in DMSO from a concentrated stock solution and then diluted in the extracellular solution.

The intracellular (pipette) solution contained: 154 mM KCl, 10 mM HEPES, 10 mM EGTA. Concentrations of $CaCl_2$ and $MgCl_2$ needed to obtain the desired free concentrations of $Ca^{2+}$ (0.3-0.4 µM, $Mg^{2+}$ always 1 mM) were calculated by EqCal software (Cambridge, UK) and added.

After establishment of the whole-cell configuration, voltage-ramps (normally −80 to +80 mV) are applied to the cell every 5 seconds from a holding potential of 0 mV. A stable baseline current is obtained within a period of 100-500 seconds, and the compound is then added by changing to an extracellular solution containing the test compound. Active compounds are quantified by calculating the change in baseline current at −75 mV. The current in the absence of compound is set to 100%. Activators will have values greater than 100, and a value of 200% indicates a doubling of the current. On the other hand, a value of 50% indicates that the compound has reduced the baseline current to half its value.

For activators a $SC_{100}$ value may be estimated. The $SC_{100}$ value is defined as the Stimulating Concentration required for increasing the baseline current by 100%. An $SC_{100}$ value below 10 µM, e.g. below 1 µM is an indication of SK3 activating properties.

Table 1 shows the result for the following compounds:

| Compound | $SC_{100}$ (µM) |
| --- | --- |
| 4 | 0.25 |
| 8.4 | 0.30 |
| 20.1 | 0.075 |

The invention claimed is:
1. A pyrazine compound of Formula I

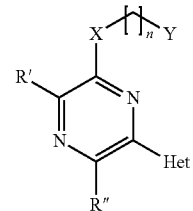

a stereoisomer thereof or a mixture of its stereoisomers, an N-oxide thereof, or a pharmaceutically acceptable salt thereof, wherein
n is 0;
X represents NH;

Y represents cycloalkyl or phenyl; which phenyl may optionally be substituted one or more times with substituents selected from the group consisting of halo and trifluoromethyl;

Het represents a heterocyclic group selected from pyrazolyl and pyrimidinyl, which pyrazolyl and pyrimidinyl may optionally be substituted one or two times with substituents selected from the group consisting of alkyl; and R' and R", independent of each other, represent hydrogen, alkyl, alkoxy-alkyl, amino, amino-alkyl, alkyl-amino, N-alkyl-amino-alkyl, or N,N-dialkyl-amino-alkyl.

2. The pyrazine compound of claim 1, a stereoisomer thereof or a mixture of its stereoisomers, an N-oxide thereof, or a pharmaceutically acceptable salt thereof, wherein Het represents pyrazolyl optionally substituted one or two times with alkyl.

3. The pyrazine compound of claim 1, a stereoisomer thereof or a mixture of its stereoisomers, an N-oxide thereof, or a pharmaceutically acceptable salt thereof, wherein Het represents pyrimidinyl.

4. The pyrazine compound of claim 1, a stereoisomer thereof or a mixture of its stereoisomers, an N-oxide thereof, or a pharmaceutically acceptable salt thereof, wherein Y represents phenyl which may optionally be substituted with halo.

5. The pyrazine compound of claim 1, a stereoisomer thereof or a mixture of its stereoisomers, an N-oxide thereof, or a pharmaceutically acceptable salt thereof wherein R' and R", independent of each other, represent hydrogen, alkyl, alkoxy-alkyl, amino, amino-alkyl, alkyl-amino, N-alkyl-amino-alkyl, or N,N-dialkyl-amino-alkyl.

6. The pyrazine compound of claim 1, which is
(4-Chloro-phenyl)-[6-(3,5-dimethyl-pyrazol-1-yl)-5-methoxymethyl-pyrazin-2-yl]-amine;
3-(4-Chloro-phenylamino)-5-(3,5-dimethyl-pyrazol-1-yl)-pyrazine-2-carbaldehyde oxime;
[5-Aminomethyl-6-(3,5-dimethyl-pyrazol-1-yl)-pyrazin-2-yl]-(4-chloro-phenyl)-amine;
N-[3-(4-Chloro-phenylamino)-5-(3,5-dimethyl-pyrazol-1-yl)-pyrazin-2-ylmethyl]-acetamide;
N-[5-(4-Chloro-phenylamino)-3-(3,5-dimethyl-pyrazol-1-yl)-pyrazin-2ylmethyl]acetamide;
5-(4-Chloro-phenylamino)-3-(3,5-dimethyl-pyrazol-1-yl)-pyrazine-2-amine; or
5-(4-Chloro-phenylamino)-3-(3,5-dimethyl-pyrazol-1-yl)-2-ethylamino-pyrazine; or a stereoisomer thereof or a mixture of its stereoisomers, an N-oxide thereof, or a pharmaceutically acceptable salt thereof.

7. The pyrazine compound of claim 1, which is
(4-Chloro-phenyl)-[6-pyrazol-1-yl-pyrazin-2-yl]amine;
Cyclohexyl-[6-(3,5-dimethyl-pyrazol-1-yl)-pyrazin-2-yl]-amine;
(4-Chloro-phenyl)-[6-(3,5-dimethyl-pyrazol-1-yl)-pyrazin-2-yl]-amine;
(4-Chloro-phenyl)-(6-pyrimidin-2-yl-pyrazin-2-yl)-amine;
(4-Chloro-phenyl)-[6-(1H-pyrazol-3-yl)-pyrazin-2-yl]-amine;
(4-Chloro-phenyl)-[3 -dimethylaminomethyl-6-(3,5-dimethyl-pyrazol -1-yl)-pyrazin-2-yl]-amine;
(4-Chloro-phenyl)-[6-(3,5-dimethyl-pyrazol-1-yl)-3-methylaminomethyl-pyrazin-2yl]-amine;
(4-Chloro-phenyl)-[5-dimethylaminomethyl-6-(3,5-dimethyl-pyrazol-1-yl)-pyrazin-2yl]-amine;
(4-Chloro-phenyl)-[6-(3,5-dimethyl-pyrazol-1-yl)-5-methylaminomethyl-pyrazin-2-yl]-amine;
(4-Chloro-phenyl)-[6-(3,5-dimethyl-pyrazol-1-yl)-3-methoxymethyl-pyrazin-2-yl]-amine; or
[3-Aminomethyl-6-(3,5-dimethyl-pyrazol-1-yl)-pyrazin-2-yl]-(4-chloro-phenyl)-amine; or
a stereoisomer thereof or a mixture of its stereoisomers, an N-oxide thereof, or a pharmaceutically acceptable salt thereof.

8. The pyrazine compound of claim 7, which is
[3-aminomethyl-6-(3,5-dimethylpyrazol-1-yl)-pyrazin-2-yl]-(4-chlorophenyl)-amine; or
a stereoisomer thereof or a mixture of its stereoisomers, an N-oxide thereof, or a pharmaceutically acceptable salt thereof.

9. A pharmaceutical composition comprising a therapeutically-effective amount of a pyrazine compound according to claim 1, a stereoisomer thereof or a mixture of its stereoisomers, an N-oxide thereof, or a pharmaceutically-acceptable addition salt thereof, together with at least one pharmaceutically-acceptable carrier or diluent.

* * * * *